(12) United States Patent
Larsen

(10) Patent No.: US 10,653,837 B2
(45) Date of Patent: May 19, 2020

(54) SYRINGE FOR RETAINING AND MIXING FIRST AND SECOND SUBSTANCES

(71) Applicant: Ferrosan Medical Devices A/S, Søborg (DK)

(72) Inventor: Kristian Larsen, Værløse (DK)

(73) Assignee: Ferrosan Medical Devices A/S, Søborg (DK)

( * ) Notice: Subject to any disclaimer, the term of this patent is extended or adjusted under 35 U.S.C. 154(b) by 101 days.

(21) Appl. No.: 15/534,801

(22) PCT Filed: Dec. 21, 2015

(86) PCT No.: PCT/EP2015/080761
§ 371 (c)(1),
(2) Date: Jun. 9, 2017

(87) PCT Pub. No.: WO2016/102446
PCT Pub. Date: Jun. 30, 2016

(65) Prior Publication Data
US 2018/0264194 A1  Sep. 20, 2018

(30) Foreign Application Priority Data
Dec. 24, 2014  (EP) .................................. 14200323

(51) Int. Cl.
*A61M 5/19*  (2006.01)
*A61M 5/24*  (2006.01)
(Continued)

(52) U.S. Cl.
CPC ............ *A61M 5/19* (2013.01); *A61M 5/2448* (2013.01); *A61M 5/31511* (2013.01);
(Continued)

(58) Field of Classification Search
CPC .. A61M 5/19; A61M 5/2488; A61M 5/31511; A61M 5/31596; A61M 5/2066; A61M 5/2053
See application file for complete search history.

(56) References Cited

U.S. PATENT DOCUMENTS 2,465,357 A   3/1949  Correll et al.
2,465,860 A   3/1949  Fleischmann
(Continued)

FOREIGN PATENT DOCUMENTS

BG   0051589   7/1993
BG   0099900   3/1997
(Continued)

OTHER PUBLICATIONS

Office Action for U.S. Appl. No. 15/639,237, titled: "Vacuum Expanded Dry Composition and Syringe for Retaining Same", dated Aug. 8, 2018.
(Continued)

*Primary Examiner* — Rebecca E Eisenberg
*Assistant Examiner* — Melissa A Snyder
(74) *Attorney, Agent, or Firm* — Hamilton, Brook, Smith & Reynolds, P.C.

(57) ABSTRACT

The present disclosure relates to a syringe for retaining and/or mixing two substances which have been retained separately inside the syringe. In particular the present disclosure relates to a syringe for 1) retaining a dry composition in a vacuum, and 2) mixing the dry composition with an aqueous medium to form a flowable substance. One embodiment relates to a syringe for mixing first and second substances comprising a barrel comprising a vacuum chamber for holding a first substance, a plunger incorporating a reservoir chamber for holding a second substance and configured to be axially displaced in the vacuum chamber, and
(Continued)

a valve for controlling and/or establishing a fluid connection between the vacuum chamber and the reservoir chamber.

24 Claims, 5 Drawing Sheets

(51) Int. Cl.
  *A61M 5/315* (2006.01)
  *A61B 17/00* (2006.01)
  *A61M 5/31* (2006.01)
(52) U.S. Cl.
  CPC .............. *A61M 5/31596* (2013.01); *A61B 2017/00495* (2013.01); *A61M 5/31501* (2013.01); *A61M 2005/3128* (2013.01)

(56) References Cited

U.S. PATENT DOCUMENTS

| | | |
|---|---|---|
| 2,507,244 A | 5/1950 | Correll |
| 2,558,395 A | 6/1951 | Studer |
| 2,899,362 A | 8/1959 | Sieger et al. |
| 3,089,815 A | 5/1963 | Kupelwieser et al. |
| 3,224,434 A | 12/1965 | Molomut et al. |
| 3,405,712 A | 10/1968 | Pierick |
| 3,514,518 A | 5/1970 | Charier-Vadrot |
| 3,608,593 A | 9/1971 | McCormick et al. |
| 3,678,933 A | 7/1972 | Moore et al. |
| 3,815,580 A | 6/1974 | Oster |
| 3,869,539 A | 3/1975 | Kring et al. |
| 3,892,876 A | 7/1975 | Hobday et al. |
| 3,899,606 A | 8/1975 | Forkner |
| 3,930,052 A | 12/1975 | De Brou et al. |
| 3,946,732 A | 3/1976 | Hurscham |
| 4,002,173 A | 1/1977 | Manning et al. |
| 4,006,220 A | 2/1977 | Gottlieb |
| 4,013,078 A | 3/1977 | Feild |
| 4,098,728 A | 7/1978 | Rosenblatt et al. |
| 4,107,288 A | 8/1978 | Oppenheim et al. |
| 4,124,705 A | 11/1978 | Rothman et al. |
| 4,150,744 A | 4/1979 | Fennimore |
| 4,160,022 A | 7/1979 | Delaney et al. |
| 4,164,559 A | 8/1979 | Miyata et al. |
| 4,179,400 A | 12/1979 | Tsao et al. |
| 4,194,392 A | 3/1980 | Lombard et al. |
| 4,208,439 A | 6/1980 | Hsu |
| 4,256,877 A | 3/1981 | Karlsson et al. |
| 4,265,233 A | 5/1981 | Sugitachi et al. |
| 4,280,954 A | 7/1981 | Yannas et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,549,554 A | 10/1985 | Markham |
| 4,554,156 A | 11/1985 | Fischer |
| 4,556,156 A | 12/1985 | Frutin |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,702,737 A | 10/1987 | Pizzino |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,887,743 A | 12/1989 | Blake et al. |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III et al. |
| 4,948,575 A | 8/1990 | Cole et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,062,834 A | 11/1991 | Gross et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |

(56) References Cited

U.S. PATENT DOCUMENTS

| | | |
|---|---|---|
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A | 7/1997 | Pruss et al. |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Ilium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,779,668 A | 7/1998 | Grabenkort |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hang et al. |
| 5,823,671 A | 10/1998 | Mitchell et al. |
| 5,824,015 A | 10/1998 | Sawyer |
| 5,853,749 A | 12/1998 | Hobbs |
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,876,372 A | 3/1999 | Seelich et al. |
| 5,883,078 A | 3/1999 | Seelich et al. |
| 5,890,610 A | 4/1999 | Jansen et al. |
| 5,895,412 A | 4/1999 | Tucker |
| 5,902,832 A | 5/1999 | Van Bladel et al. |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki et al. |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A | 5/2000 | Greenawalt et al. |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath |
| 6,129,761 A | 10/2000 | Hubbell |
| 6,132,759 A | 10/2000 | Schacht et al. |
| 6,146,587 A | 11/2000 | Morgan |
| 6,162,241 A | 12/2000 | Coury et al. |
| 6,166,130 A | 12/2000 | Rhee et al. |
| 6,168,788 B1 | 1/2001 | Wortham |
| 6,179,872 B1 | 1/2001 | Bell et al. |
| 6,193,670 B1 | 2/2001 | van Tassel et al. |
| 6,218,176 B1 | 4/2001 | Berthold et al. |
| 6,224,862 B1 | 5/2001 | Turecek et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Aiessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,321,951 B1 | 11/2001 | Frutin |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Hughes et al. |
| 6,387,413 B1 | 5/2002 | Miyata et al. |
| 6,391,343 B1 | 5/2002 | Yen |
| 6,416,739 B1 | 7/2002 | Rogerson |
| 6,423,037 B1 | 7/2002 | Hijikata et al. |
| 6,454,787 B1 | 9/2002 | Maddalo et al. |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,861,046 B1 | 3/2005 | Appino et al. |
| 6,887,974 B2 | 5/2005 | Pathak |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |
| 7,393,674 B2 | 7/2008 | Jiang et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,071,090 B2 | 12/2011 | Senderoff et al. |
| 8,119,160 B2 | 2/2012 | Looney et al. |
| 8,303,981 B2 | 11/2012 | Wallace et al. |
| 8,329,119 B2 | 12/2012 | Pearcy et al. |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,556,848 B2 | 10/2013 | Klug et al. |
| 8,603,511 B2 | 12/2013 | Wallace et al. |
| 8,642,831 B2 | 2/2014 | Larsen et al. |
| 8,846,105 B2 | 9/2014 | Koopman et al. |
| 9,265,858 B2 | 2/2016 | Larsen |
| 9,376,674 B2 | 6/2016 | Jorquera Nieto et al. |
| 9,408,945 B2 | 8/2016 | Goessl et al. |
| 9,533,069 B2 | 1/2017 | Larsen et al. |
| 9,629,798 B2 | 4/2017 | Senderoff et al. |

(56) References Cited

U.S. PATENT DOCUMENTS

| | | |
|---|---|---|
| 9,724,078 B2 | 8/2017 | Larsen et al. |
| 9,999,703 B2 | 6/2018 | Larsen |
| 10,111,980 B2 | 10/2018 | Larsen |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | de LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0082620 A1 | 6/2002 | Lee et al. |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0040701 A1* | 2/2003 | Dalmose ........... A61M 5/31596 604/87 |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0175410 A1 | 9/2003 | Campbell |
| 2003/0175419 A1 | 9/2003 | Sessa |
| 2003/0181659 A1 | 9/2003 | Naranda et al. |
| 2003/0224056 A1 | 12/2003 | Kotha et al. |
| 2003/0225378 A1 | 12/2003 | Wilkie et al. |
| 2003/0232746 A1 | 12/2003 | Lamberti et al. |
| 2004/0062790 A1 | 4/2004 | Constantine et al. |
| 2004/0076647 A1 | 4/2004 | Biering |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0186432 A1* | 9/2004 | Barry ................ A61M 5/30 604/152 |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2004/0267352 A1 | 12/2004 | Davidson et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0186253 A1 | 8/2005 | Lee et al. |
| 2005/0214277 A1 | 9/2005 | Schaufler |
| 2005/0218541 A1 | 10/2005 | Peng et al. |
| 2005/0239675 A1 | 10/2005 | Makansi |
| 2005/0245905 A1 | 11/2005 | Schmidt et al. |
| 2005/0284809 A1 | 12/2005 | Looney et al. |
| 2006/0002890 A1 | 1/2006 | Hersel et al. |
| 2006/0002918 A1 | 1/2006 | Jiang et al. |
| 2006/0052747 A1 | 3/2006 | Nishimura et al. |
| 2006/0067976 A1 | 3/2006 | Ferraro et al. |
| 2006/0068013 A1 | 3/2006 | DiTizio et al. |
| 2006/0115805 A1 | 6/2006 | Hansen |
| 2006/0121080 A1 | 6/2006 | Lye et al. |
| 2006/0121104 A1 | 6/2006 | Stern |
| 2006/0147492 A1 | 7/2006 | Hunter et al. |
| 2006/0159733 A1 | 7/2006 | Pendharkar et al. |
| 2006/0167561 A1 | 7/2006 | Odar et al. |
| 2006/0189516 A1 | 8/2006 | Yang et al. |
| 2006/0193846 A1 | 8/2006 | Stimmeder |
| 2006/0204490 A1 | 9/2006 | Pendharkar et al. |
| 2006/0255053 A1 | 11/2006 | Li |
| 2006/0282138 A1 | 12/2006 | Ota |
| 2007/0009578 A1 | 1/2007 | Moiler et al. |
| 2007/0025955 A1 | 2/2007 | Lowinger et al. |
| 2007/0054020 A1 | 3/2007 | Kumagai |
| 2007/0086958 A1 | 4/2007 | Drake et al. |
| 2007/0128343 A1 | 6/2007 | Chappa |
| 2007/0160543 A1 | 7/2007 | Moiler |
| 2007/0215235 A1 | 9/2007 | Ranalletta et al. |
| 2007/0250007 A1 | 10/2007 | Shekalim |
| 2007/0264130 A1 | 11/2007 | Mallett |
| 2007/0264301 A1 | 11/2007 | Cleek et al. |
| 2007/0264302 A1 | 11/2007 | Cleek et al. |
| 2008/0029087 A1 | 2/2008 | Kidd, III |
| 2008/0085316 A1 | 4/2008 | Qian et al. |
| 2008/0091277 A1 | 4/2008 | Deusch et al. |
| 2008/0095830 A1 | 4/2008 | Van Holten |
| 2008/0109002 A1 | 5/2008 | Delmotte |
| 2008/0199539 A1 | 8/2008 | Baker et al. |
| 2008/0286376 A1 | 11/2008 | Qian et al. |
| 2008/0311172 A1 | 12/2008 | Schapira et al. |
| 2009/0087569 A1 | 4/2009 | Fan et al. |
| 2009/0142396 A1 | 6/2009 | Odar et al. |
| 2009/0157017 A1 | 6/2009 | Ambrosio |
| 2010/0028309 A1 | 2/2010 | Odar et al. |
| 2010/0048758 A1 | 2/2010 | Chen et al. |
| 2010/0063459 A1 | 3/2010 | Preiss-Bloom et al. |
| 2010/0113828 A1 | 5/2010 | Dalsin et al. |
| 2010/0143447 A1 | 6/2010 | Hansen |
| 2010/0256671 A1 | 10/2010 | Falus |
| 2010/0292717 A1 | 11/2010 | Petter-Puchner et al. |
| 2010/0318048 A1 | 12/2010 | Hoeffinghoff et al. |
| 2011/0021964 A1 | 1/2011 | Larsen et al. |
| 2011/0045034 A1 | 2/2011 | Nur et al. |
| 2011/0059228 A1 | 3/2011 | Gillick et al. |
| 2011/0270167 A1 | 11/2011 | Matusch |
| 2012/0128653 A1 | 5/2012 | Goessl et al. |
| 2012/0201726 A1 | 8/2012 | Pearcy et al. |
| 2014/0220130 A1 | 8/2014 | Larsen et al. |
| 2015/0037314 A1 | 2/2015 | Larsen |
| 2015/0045830 A1 | 2/2015 | Jensen et al. |
| 2016/0120527 A1 | 5/2016 | Larsen et al. |
| 2016/0354512 A1 | 12/2016 | Larsen |
| 2017/0311939 A1 | 11/2017 | Larsen et al. |
| 2018/0147355 A1 | 5/2018 | Larsen |
| 2018/0243468 A1 | 8/2018 | Larsen |
| 2019/0015546 A1 | 1/2019 | Larsen |

FOREIGN PATENT DOCUMENTS

| | | |
|---|---|---|
| CN | 1270240 | 10/2000 |
| DE | 2316209 A1 | 10/1974 |
| DE | 3146841 | 6/1983 |
| DE | 4119140 | 12/1992 |
| DE | 4407875 | 9/1995 |
| EP | 0132983 | 2/1985 |
| EP | 0156649 | 10/1985 |
| EP | 0282316 | 9/1988 |
| EP | 0341007 | 11/1989 |
| EP | 0341745 | 11/1989 |
| EP | 0365705 | 5/1990 |
| EP | 0372966 | 6/1990 |
| EP | 0385916 A2 | 9/1990 |
| EP | 0395758 | 11/1990 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |

(56) References Cited

FOREIGN PATENT DOCUMENTS

| | | |
|---|---|---|
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1095064 | 6/2005 |
| EP | 1543842 A1 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| EP | 2 040 724 B1 | 10/2011 |
| FR | 2679772 | 5/1993 |
| FR | 2759980 | 8/1998 |
| GB | 648619 | 1/1951 |
| GB | 697603 | 9/1953 |
| GB | 1037937 | 8/1966 |
| GB | 1199887 | 7/1970 |
| GB | 1 483 002 | 7/1975 |
| GB | 1584080 | 2/1981 |
| GB | 1591654 | 6/1981 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 01130519 | 5/1989 |
| JP | 05308969 | 11/1993 |
| JP | 06254148 | 9/1994 |
| JP | H07090241 | 4/1995 |
| JP | 08-024325 | 1/1996 |
| JP | 9-504719 | 5/1997 |
| JP | 10-507666 | 7/1998 |
| JP | 2002/513308 | 5/2002 |
| JP | 2004002271 | 1/2004 |
| JP | 2004147959 | 5/2004 |
| JP | 2006-296896 | 11/2006 |
| JP | 2010228932 | 10/2010 |
| JP | 2011212182 A | 10/2011 |
| KR | 910007847 | 10/1991 |
| KR | 100751046 | 8/2007 |
| WO | WO 83/01244 | 4/1983 |
| WO | WO 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |
| WO | WO 99/38606 | 8/1999 |
| WO | WO 99/44901 | 9/1999 |
| WO | WO 99/45938 | 9/1999 |
| WO | WO 99/051208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | 01/97871 A2 | 12/2001 |
| WO | 0197871 A2 | 12/2001 |
| WO | WO 01/97826 | 12/2001 |
| WO | WO 02/18450 | 3/2002 |
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | 02/072128 A1 | 9/2002 |
| WO | 02072128 A1 | 9/2002 |
| WO | WO 02/070594 | 9/2002 |
| WO | 02096488 A1 | 12/2002 |
| WO | WO 03/007845 | 1/2003 |
| WO | WO 2003/004072 | 1/2003 |
| WO | WO 03/024426 | 3/2003 |
| WO | WO 03/024429 | 3/2003 |
| WO | WO 03/055531 | 7/2003 |
| WO | WO 2003/070110 | 8/2003 |
| WO | WO 03/074103 A2 | 9/2003 |
| WO | WO 03/094983 | 11/2003 |
| WO | WO 04/028404 | 4/2004 |
| WO | WO 04/028423 | 4/2004 |
| WO | WO 04/029095 | 4/2004 |
| WO | WO 04/030711 | 4/2004 |
| WO | WO 2004/026377 A1 | 4/2004 |
| WO | WO 2004/028583 | 4/2004 |
| WO | WO 2004/035629 | 4/2004 |
| WO | WO 2004/053051 | 6/2004 |
| WO | WO 2004/069303 A2 | 8/2004 |
| WO | WO 04/075650 | 9/2004 |
| WO | WO 04/084869 | 10/2004 |
| WO | WO 04/108035 | 12/2004 |
| WO | WO 2004/108179 | 12/2004 |
| WO | WO 2004/108418 A1 | 12/2004 |
| WO | 2005/002510 A2 | 1/2005 |
| WO | 2005002510 A2 | 1/2005 |
| WO | WO 05/000265 | 1/2005 |
| WO | WO 05/009225 | 2/2005 |
| WO | WO 05/041811 | 5/2005 |
| WO | WO 05/044285 | 5/2005 |
| WO | WO 05/062889 | 7/2005 |
| WO | WO 05/063217 A1 | 7/2005 |
| WO | WO 2005/072700 | 8/2005 |
| WO | WO 2005/084650 A1 | 9/2005 |
| WO | WO 05/107713 | 11/2005 |
| WO | WO 2006/005340 | 1/2006 |
| WO | WO 2006/031358 | 3/2006 |
| WO | WO 06/034568 | 4/2006 |

(56) References Cited

FOREIGN PATENT DOCUMENTS

| WO | 2006/063758 | 6/2006 |
|---|---|---|
| WO | WO 06/063758 | 6/2006 |
| WO | WO 06/128471 | 12/2006 |
| WO | WO 2007/001926 | 1/2007 |
| WO | WO 2007/018887 A2 | 2/2007 |
| WO | WO 2007/092618 A2 | 8/2007 |
| WO | WO 2007/133699 | 11/2007 |
| WO | WO 2007/137839 | 12/2007 |
| WO | 2008019127 A2 | 2/2008 |
| WO | WO 2008/016983 | 2/2008 |
| WO | 2008060475 A2 | 5/2008 |
| WO | WO 2008/051758 | 5/2008 |
| WO | WO 2008/090555 | 7/2008 |
| WO | WO 2009/020612 | 2/2009 |
| WO | WO 2009/109194 | 9/2009 |
| WO | WO 2009/109963 | 9/2009 |
| WO | WO 2009/131752 A2 | 10/2009 |
| WO | WO 2011/047753 A1 | 4/2011 |
| WO | WO 2011/137437 A2 | 11/2011 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/112579 A1 | 8/2013 |
| WO | WO 2013/131520 A2 | 9/2013 |
| WO | WO 2013/185776 A1 | 12/2013 |
| WO | WO 2014/086996 | 6/2014 |
| WO | WO 2014/0202760 A2 | 12/2014 |
| WO | WO 2015/086028 A1 | 6/2015 |
| WO | WO 2016/058612 A1 | 4/2016 |
| WO | 2017/005590 | 1/2017 |
| WO | WO 2017/098493 A1 | 6/2017 |

OTHER PUBLICATIONS

Final Office Action for U.S. Appl. No. 15/639,237, titled: "Vacuum Expanded Dry Composition and Syringe for Retaining Same", dated Nov. 30, 2018.
Final Office Action for U.S. Appl. No. 14/383,461, titled: "Pressurized Container Containing Haemostatic Paste", dated Jan. 8, 2019.
Office Action for U.S. Appl. No. 15/639,237, titled: "Vacuum Expanded Dry Composition and Syringe for Retaining Same", dated May 8, 2019.
Schreiber, M.A., et al., "Achieving Hemostasis with Topical Hemostats: Making Clinically and Economically Appropriate Decisions in the Surgical and Trauma Settings", AORN Journal, 94(5): S1-S20 (2011).
Non-Final Office Action for U.S. Appl. No. 14/980,254, titled: "Dry Haemostatic Composition", dated May 8, 2017.
Final Office Action for U.S. Appl. No. 14/383,461, titled: "Pressurized Container Containing Haemostatic Paste", dated Dec. 14, 2017.
"Formulation and Evaluation of Absorbable Gelatin Sponges," Chapter 3A of Rupali Kale thesis: Design and Development of Surgical Dressings for Advanced Wound Management (2010).
"Gelfoam Prescribing Information," Pharmacia & Upjohn (Nov. 1996).
"Gelfoam® Product Brochure," Pharmacia & Upjohn (Jun. 2013).
26th Annual Symposium: Clinical Update in Anaesthesiology, Surgery and Perioperative Medicine, Jan. 20-25, 2008.
Ansell, J., et al., "Gelfoam and Autologous Clot Embolization: Effect on Coagulation," Investigative Radiology, 13: 115-120 (1978).
Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy "concise explanation" requirement under 37 C.F.R. 1.98(a)(3)).

Barrow, D.L., et al., "The Use of Greater Omentum Vascularized Free Flaps for Neurosurgical Disorders Requiring Reconstruction", Journal of Neurosurgery, 60: 305-311 (1984).
Barton, B., et al., "Fibrin Glue as a Biologic Vascular Patch—A Comparative Study," Journal of Surgical Research, vol. 40, 1 page; abstract retrieved from http://www.ncbi.nlm.nih.gov on Jan. 3, 2001. (1986).
Baxter, "GentaFleece Collagen Fleece—Version 5: Instructions for Use—Collagen Sponge with Antibiotic Protection for Surgical Use," Retrieved from http://www.advancingbiosurgery.com/en_EU/downloads/ifu_gentafleece.pdf on Mar. 2002, 2 pages. English portion second column of first page.
Baxter, "Product Catalogue: Collagen," 4 pages, retrieved from http://www.baxter-ecommerce.com/ecatalog on Feb. 2, 2006 (2006).
Baxter, "TissuFleece E Package Leaflet," Baxter International Inc., 4 pages, English portion of instructions for use (2003).
Baxter, "TissuFleece E, TissuCone E and TissuFoil E: Biomaterials," Basic scientific Information, 9 pages (2003).
Boland, T., et al., "Application of Inkjet Printing to Tissue Engineering," Biotechnol. J., 1: 910-917 (2006).
Boyers, S., et al., "Reduction of Postoperative Pelvic Adhesions in the Rabbit with Gore-Tex Surgical Membrane", Fertility and Sterility, 49(6,): 1066-1070 (1988).
Brannon-Peppas, L., et al., "The Equilibrium Swelling Behavior of Porous and Non-Porous Hydrogels," Absorbent Polymer Technology, Elsevier, Amsterdam, pp. 67-102 (1990).
Branski, R.C., et al., "Mucosal Wound Healing in a Rabbit Model of Subglottic Stenosis"; Arch Otolaryngol Head Neck Surg, vol. 131, Feb. 2005, p. 153-157.
Brunt and Klausner, "Growth factors speed wound healing", Nature Biotechnology, 6(1): 25-30 (1988).
Campbell, P.G., et al., "Engineered Spatial Patterns of FGF-2 Immobilized on Fibrin Direct Cell Organization," Biomaterials, 26: 6762-6770 (2005).
Campbell, P.G., et al., "Tissue Engineering with the Aid of Inkjet Printers," Expert Opin. Biol. Ther., 7: 1123-1127 (2007).
Canal, T., et al., "Correlation Between Mesh Size and Equilibrium Degree of Swelling of Polymeric Networks" Biomedical Materials Research, 23: 1183-1193 (1989).
Cantor, M.O., et al., "Gelfoam® and Thrombin in treatment of massive gastroduodenal hemorrhage—A preliminary report", American Journal of Surgery, 883-887 (Dec. 1950).
Cantor, M.O., et al., "Gelfoam and Thrombin in Gastroduodenal Bleeding: An Experimental Study," Journal of Laboratory and Clinical Medicine, 35(6): 890-893 (1950).
Cantor, M.O., et al., "Gelfoam and Thrombin in Treatment of Massive Upper Gastrointestinal Hemorrhage," American Journal of Surgery, 82(2): 230-235 (Aug. 1951).
Cascone, M.G., et al., "Collagen and hyaluronic acid based polymeric blends as drug delivery systems for the release of physiological concentrations of growth hormone." Journal of Materials science: Materials in Medicine; 5: 770-774 (1994).
Changez, M., et al., Abstract of "Efficacy of antibiotics-loaded interpenetrating network (IPNs) hydrogel based on poly (acrylic acid) and gelatin for treatment of experimental osteomyelitis: in vivo study.", Biomaterials; 26(14): 2095-2104 (2005).
Chaplin, J .M., et al., "Use of an Acellular Dermal Allograft for Dural Replacement: An Experimental Study," Neurosurgery, 45(2): 320-327 (1999).
Cheung, D., et al., "Mechanism of Crosslinking of Proteins by Glutaraldehyde IV: In Vitro and In Vivo Stability of a Crosslinked Collagen Matrix," Connective Tissue Research, 25: 27-34 (1990).
Choi, Y.S., et al., "Studies on Gelatin-Based Sponges. Part I11: A Comparative Study of Cross-linked Gelatin/ Alginate, Gelatin/Hyaluronate and Chitosan/Hyaluronate Sponges and their Application as a wound dressing in fullthickness skin defect of rat.", J. Of Mat. Sci.; Mat. In Med.; 12: 67-73 (Jan. 2001).
Choi, Y.S., et al., "Studies on gelatin-containing artificial skin: II. Preparation and characterization of cross-linked gelatin-hyaluronate sponge.", J. Biomed Mater Res., 48: 631-639 (1999).
Christensen, F, et al., "Qualitative Description of the Wurster-Based Fluid-Bed Coating Process," Drug Dev and Industry Pharmacy, 23(5): 451-463 (1977).

(56) References Cited

OTHER PUBLICATIONS

Chronic Wound Care Guidelines © 2007 http://woundheal.org. documents/final_pocket_guide_treatment.aspx.
Chuang, V.P., et al., "Sheath Needle for Liver Biopsy in High-Risk Patients" Radiology, 166: 261-262 (1988).
Coenye, K.E., et al., "A Qualitative Morphological comparison of Two Heamostatic Agents in a Porcine Liver Trauma Model," Surgical Science, 4: 359-364 (2013).
Collins, D., et al., "Enemata of Gelfoam Milk Suspension Combined with Thrombin-Solution to Control Massive Hemorrhage Following Anorectal Surgery," The American Journal of Proctology, 2: 60-63 (1951).
Collins, R., et al., "Use of Collagen Film as a Dural Substitute: Preliminary Animal Studies," Journal of Biomedical Materials Research, 25: 267-276 (1991).
De la Torre, R.A., et al., "Hemostasis and Hemostatic agents in minimally invasive surgery", Surgery, 142(4S): S39-S45 (2007).
De Iaco, P.A., et al., "Efficacy of a Hyaluronan Derivative gel in postsurgical adhesion prevention in the presence of inadequate hemostasis." Surgery, 130(1): 60-64 (2001).
DeLustro, F., et al., "A Comparative Study of the Biologic and Immunologic Response to Medical Devices Derived From Dermal Collagen," Journal of Biomedical Materials Research, 20: 109-120 (1986).
Dembo, M.A., et al., Abstract of "Antiseptic hemostatic preparations, their properties and study", Lech. Prep. Krovi Tkanei; pp. 139-140 (1974).
Dodd, G.D., et al., "Minimally invasive treatment of malignant hepatic tumors. At the threshold of a major breakthrough", Radiographies, 20: 9-27 (2000).
Drognitz, O., et al., Abstract of "Release of vancomycin and teicoplanin from a plasticized and resorbable gelatin sponge: in vitro investigation of a new antibiotic delivery system with glycopeptides"; Indection Germany (Minich); 34(1): 29-34 (2006).
Duchene, D., et al., "Pharmaceutical and Medical Aspects of Bioadhesive Systems for Drug Administration," Drug Dev and Industr Pharmacy, 14(2&3):283-318 (1988).
Edgerton, M., et al., "Vascular Hamatomas and Hemagiomas: Classification and Treatment," Southern Medical Journal, 75(12): 1541-1547 (1982).
Ellegala, D.B., et al., "Use of FloSeal Hemostatic Sealant in Transsphenoidal Pituitary Surgery: Technical Note."; Neurosurgery, 51: 513-516 (Aug. 2002).
English Derwent Abstract of Ranjane reference, Nov. 18, 1997.
Filippi, R., et al., "Bovine Pericardium for Duraplasty: Clinical Results in 32 Patients," Neurological Review, 20:103-107 (2001).
Final Office Action for U.S. Appl. No. 14/136,578, titled: "Device for Promotion of Hemostasis and/or Wound Healing", dated Feb. 26, 2015 "Dry Haemostatic Composition".
Final Office Action for U.S. Appl. No. 14/136,578, titled: "Device for Promotion of Hemostasis and/or Wound Healing", dated Oct. 29, 2015.
Fiss, I., et al., "Use of Gelatin-Thrombin Hemostatic Sealant in Cranial Neurosurgery," Neurologia Medico-Chirurgica, 47(10):462-467 (2007).
Flory, P., "Phase Equilibria in Polymer Systems," Principles of Polymer Chemistry, 13: 541-594 (1953).
FloSeal Matrix Hemostatic Sealant, Instructions for Use, Retrieved from Internet URL http://www.ctsnet.org/file/vendors/931/pdf/140. pdf [retrieved on Aug. 17, 2005].
Fujii, Y., et al., "Safety of GT XIII (Report 2)—Japanese + English translation," The Clinical Report, 20(17) (Dec. 1986).
Gall, R.M., "Control of Bleeding in Endoscopic Sinus Surgery: Use of a Novel Gelatin-Based Hemostatic Agent", Journal of Otolaryngology, 31(5): (2002).
Gelfoam absorbable powder. Retrieved from Internet URL: http://www.fda.gov/cdrh/pdf/N18286S012c.pdf [retrieved on May 22, 2009].
Gibble, J.W., et al., "Fibrin glue: the perfect operative sealant?" Reviews: Transfusion, 30(8): 741-747 (1990).
Guinto, F., "Preparation of Gelfoam Particles Using an Orthopedic Rasp," Radiology, 153: 250 (1984).
Gurny, R., et al.,"Bioadhesive Intraoral Release Systems: Design, Testing and Analysis," Biomaterials, 5: 336-340 (1984).
Hae-Won, K., et al., Abstract of "Porus scaffolds of gelatin-hydroxyapatite nanocomposites obtained by biometic approach: Characterization and antibiotic drug release."; J. of Biomedical Materials Research, 74B(2): 686-698 (2005).
Harris, W.H., et al., "Topical Hemostatic Agents for Bone Bleeding in Humans," The Journal of Bone and Joint Surgery, 60-A(4): 454-456 (1978).
Heller, J., et al., "Release of Norethindrone from Poly(Ortho Esters)," Polymer Engineering and Science, 21: 727-731 (1981).
Herndon, J., et al., "Compression of the Brain and Spinal Cord Following Use of Gelfoam," Arch. Surg, 104: 107 (Jan. 1972).
Hieb, L., et al, "Spontaneous Postoperative Cerebrospinal Fluid Leaks Following Application of Anti-Adhesion Barrier Gel," SPINE, 26(7): 748-751 (2001).
Hill, et al., "Use of microfibrillar collagen hemostat (avitenet) and thrombin to achieve hemostats after median sternotomy."; J. Thorac Cardiovasc Surg., 108: 1151-1152 (1994).
Hill-West, J.L., et al., "Efficacy of a resorbable hydrogel barrier, oxidized regenerated cellulose and hyaluronic acid in the prevention of ovarian adhesions in a rabbit model."; Fertility and Sterility, 62(3): 630-634 (1994).
Hong, S.R., et al., Abstract of "Study on gelatin-containing artificial skin IV: a comparative study on the effect of antibiotic and EGF on cell proliferation during epidermal healing."; Biomaterials, 22(20): 2777-2783 (2001).
Hong, Y.M., et al., "The Use of Hemostatic Agents and Sealants in Urology", The Journal of Urology, 176: 2367-2374 (2006).
Hood, D., et al., "Efficacy of Topical Hemostat Floseal Matrix in Vascular Surgery," 24th World Congress of the International Society for Cardiovascular Surgery, Sep. 12-16, 1999, 2 pages.
Hotz, G., et al., "Collagen and Fibrin as Biologic Binders from Granular Hydroxyapatite," Deutsche Zeitschrift fur Mund-Kieferund Gesichts-Chirurgie, 13(4): 296-300 (1989). Abstract retrieved from http://www.ncbi.nlm.nih.gov on Jan. 3, 2001.
International Preliminary Examination Report for International Application No. PCT/DK03/00855, "Gelatine-Based Materials As Swabs", completed Jun. 2, 2005.
International Preliminary Report on Patentability (Corrected Version) for International Application No. PCT/DK2005/000063, "Haemostatic Sprays and Compositions", completed Nov. 6, 2006.
International Preliminary Report on Patentability for International Application No. PCT/DK2005/000475, "Haemostatic Composition Comprising Hyaluronic Acid", completed Aug. 16, 2006.
International Preliminary Report on Patentability for International Application No. PCT/DK2007/050196, "Wound or Tissue Dressing Comprising Lactic Acid Bacteria", completed May 29, 2009.
International Preliminary Report on Patentability for International Application No. PCT/DK2009/050048, "Device for Promotion of Hemostasis and/or Wound Healing", completed Sep. 6, 2010.
International Preliminary Report on Patentability for International Application No. PCT/DK2013/050054, "Pressurized Container Containing Haemostatic Paste", dated Sep. 9, 2014.
International Preliminary Report on Patentability from counterpart International Application No. PCT/DK2011/050082, "A Method for Promotion of Hemostasis and/or Wound Healing", dated Jul. 6, 2012.
International Search Report & Written Opinion of the International Searching Authority for International Application No. PCT/DK2007/050196, "Wound or Tissue Dressing Comprising Lactic Acid Bacteria", dated Apr. 23, 2008.
International Search Report and Written Opinion of the International Searching Authority from counterpart International Application No. PCT/DK2011/050082, "A Method for Promotion of Hemostasis and/or Wound Healing", dated Jun. 21, 2011.
International Search Report for International Application No. PCT/DK2003/000855, "Gelatine-Based Materials as Swabs", dated Oct. 8, 2004.
International Search Report for International Application No. PCT/DK2005/000063, "Haemostatic Sprays and Compositions".

(56) References Cited

OTHER PUBLICATIONS

International Search Report for International Application No. PCT/DK2005/000475, "Haemostatic Composition Comprising Hyaluronic Acid", dated Oct. 25, 2005.
International Search Report for International Application No. PCT/DK2009/050048, "Device for Promotion of Hemostasis and/or Wound Healing", dated Apr. 6, 2010.
International Search Report for International Application No. PCT/DK2013/050054, "Pressurized Container Containing Haemostatic Paste", dated Sep. 10, 2013.
International Search Report for International Application No. PCT/DK2013/050191, "Dry Haemostatic Composition", dated Aug. 21, 2013.
Jeong, B., et al., "Biodegradable Block Copolymers as Injectable Drug-Delivery Systems," Nature, 388: 860-862 (1997).
Jonas, R., et al., "A new sealant for knitted Dacron prostheses: Minimally cross-linked gelatin," Journal of Vascular Surgery, 7(3): 414-419 (1988).
Katayama, T., et al., "GT XIII safety (3rd report)—Japanese + English translation," The Clinical Report, vol. 20 (1986).
Kelly M.J. et al., "The value of an operative wound swab sent in transport medium in the prediction of later clinical wound infection: A controlled clinical and bacteriological evaluation.", Brit. J. Surgery, 65: 81-88 (1978).
Kim, K., et al., "Reduction in Leg Pain and Lower-Extremity Weakness with Oxiplex/SP Gel for 1 Year after Laminevtomy, Laminotomy, and Disectomy," Neurosurgical Focus, 17: 1-6 (2004).
Kline, D., et al., "Dural Replacement with Resorbable Collagen," Archives of Surgery, 91: 924-929 (1965).
Knopp, U., "A New Collagen Foil Versus a Cadaveric Dura Graft for Dural Defects—A Comparative Animal Experimental Study," European Association of Neurosurgical Societies—Proceedings of the 12th European Congress of Neurosurgery, Lisbon, 17 pages (2003).
Koçak, I., et al., "Reduction of adhesion formation with cross-linked hyaluronic acid after peritoneal surgery in rats.", Fertility and Sterility, 72(5): 873-878 (1999).
Kofidis, T., et al., "Clinically Established Hemostatis Scaffold (Tissue Fleece) as Biomatrix in Tissue and Organ Engineering Research," Tissue Engineering, 9: 517-523 (2003).
Kost J., and Langer R., "Equilibrium Swollen Hydrogels in Controlled Release Applications," Ch. 5: Hydrogels in Medicine and Pharmacy, vol. III: properties and Applications, N. Peppas ed., pp. 95-108 (1987).
Krill, D., et al., "Topical Thrombin and Powdered Gelfoam: An Efficient Hemostatic Treatment for Surgery," Journal of Tennessee Dental Association, 66(2): 26-27 (1986).
Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," Journal of Neurology, Neurosergery & Psychiatry, 76: 1031-1033 (2005).
Langer, R., et al., "Chemical and Physical Structure of Polymers as Carriers for Controlled Release of Bioactive Agents: A Review," Journal of Macromolecular Science-Reviews in Macromolecular Chemistry and Physics, C23: 61-126 (1983).
Laquerriere, A., et al., "Experimental Evaluation of Bilayered Human Collagen as a Dural Substitute," Journal of Neurosurgery, 78: 487-491 (1993).
Larson, P., "Topical Hemostatic Agents for Dermatologic Surgery," Journal of Dermatologic Surgery & Oncology, 14: 623-632 (1988).
Larsson, B., et al., "Surgicel®—an absorbable hemostatic material-in prevention of peritoneal adhesion in rats."; Acta Chir Scand., 26(144): 375-378 (1978).
Laurent, C., et al., "Hyaluronic acid reduces connective tissue formation in middle ears filled with absorbable gelatin sponge: An experimental study.", AM. J.Otolaryngol, 7: 181-186 (1986).
Le, A., et al., "Unrecognized Durotomy After Lumbar Discectomy: A Report of Four Cases Associated with the Use of ADCON-L," Spine, 26(1): 115-118 (2001).
Lee, J., et al., "Experimental Evaluation of Silicone-Coated Dacron and Collagen Fabric-Film Laminate as Dural Substitutes," Journal of Neurosurgery, 27: 558-564 (1967).
Lee, P., "Interpretation of Drug-Release Kinetics from Hydrogel Matrices in Terms of Time-Dependent Diffusion Coefficients," Controlled-Release Technology—Pharmaceutical Applications, Ch. 5, ACS Symposium Series 348, pp. 71-83 (1986).
Leong, K., et al., "Polyanhydrides for Controlled Release of Bioactive Agents," Biomaterials, 7: 364-371 (1986).
Leong, K., et al., "Polymeric Controlled Drug Delivery," Advanced Drug Delivery Reviews, 1: 199-233 (1987).
Lewis, K., et al., "Comparison of Two Gelatin and Thrombin Combination Hemostats in a Porcine Liver Abrasion Model," Journal of Investigative Surgery, 26: 141-148 (2013).
Li, G., et al., "Evaluation of esterified hyaluronic acid as middle ear-packing material.", Arch Otolaryngol Head Neck Surg, 127: 534-539 (2001).
Loeb, J, "The Influence of Electrolytes Upon the Osmotic Pressure of Gelatin Solutions", J. Biol. Chem., 35: 497-508 (1918).
Luengo, J., et al., "Prevention of peritoneal adhesions by the combined use of Spongostan and 32% Dextran 70: An experimental study in pigs." Fertility and Sterility, 29(4): 447-450 (1978).
Masar, E., et al., "Synthesis of Polyurethanes and Investigation of their Hydrolytic Stability," Journal of Polymer Science: Polymer Symposium, 66: 259-268 (1979).
Masuzawa, M., et al., "Experimental Study Related to the Hemostasis Action of GT XIII," The Clinical Report, 20(2): 471-476 (Feb. 1986).
Matsumoto, K., et al., "A Gelatin Coated Collagen-Polyglycolic Acid Composite Membrane as a Dural Substitute," American Society for Artificial Internal Organs Journal, 47: 641-645 (2001).
Maurer, P, et al., "Vicryl (Polyglactin 910) Mesh as a Dural Substitute," Journal of Neurosurgery, 63:448-452 (1985).
Maxson, W.S., et al., "Efficacy of a modified oxidized cellulose fabric in the prevention of adhesion formation." Gynecol. Obstet. Invest., 26: 160-165 (1988).
McClure, J., et al., "Massive Gastroduodenal Hemorrhage: Treatment with Powdered Gelfoam and Buffered Thrombin Solution," Surgery, 32: 630-637 (1952).
McPherson, J., et al., "An Examination of the Biologic Response to Injectable, Glutaraldehyde Cross-linked Collagen Implants," Journal of Biomedical Materials Research, 20: 93-107 (1986).
McPherson, J., et al., "Development and Biochemical Characterization of Injectable Collagen," J. Dermatol. Surg. Oncol., 12(1): 13-20 (Jul. 7, 1988).
McPherson, J., et al., "The Effects of Heparin on the Physiochemical Properties of Reconstituted Collagen," Collagen and Related Research, 1: 65-82 (1988).
McPherson, J., et al., "The Preparation and Physiochemical Characterization of an Injectable Form of Reconstituted, Glutaraldehyde Crosslinked, Bovine Corium Collagen," Journal of Biomedical Materials Research, 20: 79-92 (1986).
Meddings, N., et al., "Collagen Vicryl-A New Dural Prosthesis," Acta Neurochirurgica, 117: 53-58 (1992).
Mello, L., et al., "Duraplasty with Biosynthetic Cellulose: An Experimental Study," Journal of Neurosurgery, 86: 143-150 (1997).
Miller, D., and Peppas, N., "Diffusional Effects During Albumin Adsorption on Highly Swollen Poly(vinyl Alcohol) Hydrogels," Eur. Polym. J., 24(7): 611-615 (1988).
Miller, E.D., et al., "Dose-Dependent Cell Growth in Response to Concentration Modulated Patterns of FGF-2 Printed on Fibrin," Biomaterials, 27: 2213-2221 (2006).
Millikan, L., "Treatment of Depressed Cutaneous Scars with Gelatin Matrix Implant: A Multicenter Study," J. Am. Acad. Dermatol., 16: 1155-1162 (1987).
Min et al., "Molecular Weight Changes of Sodium Hyaluronate Powder and Solution by Heat treatment," Matrix Biology Institute, Proceedings of Hyaluronan, Oct. 11-16, 2003.
Mitsuhashi, J., "Invertabrate Tissue Culture Methods," Springer Lab Manual, p. 407 (2002).
Moak, E., "Hemostatic Agents: Adjuncts to Control Bleeding," Today's O.R. Nurse, pp. 6-10 (1991).

(56) References Cited

OTHER PUBLICATIONS

Mueller, K., "Release and Delayed Release of Water-Soluble Drugs from Polymer Beads with Low Water Swelling," Controlled-Release Technology—Pharmaceutical Applications, Ch. 11, ACS Symposium Series, 348: 139-157 (1986).

Muranyi, et al., "Development of gel-forming lyophilized formulation with recombinant human thrombin", Drug Development and Industrial Pharmacy 41(9): (2015) 1566-1573. (Abstract Only).

Narotam, P., et al., "A Clinicopathological Study of Collagen Sponge as a Dural Graft in Neurosurgery," Journal of Neurosurgery, 82: 406-412 (1995).

Narotam, P., et al., "Experimental Evaluation of Collagen Sponge as a Dural Graft," British Journal of Neurosurgery, 7: 635-641 (1993).

Nimni, M., et al., "Chemically Modified Collagen: A Natural Biomaterial for Tissue Replacement," Journal of Biomedical Materials Research, 21: 741-771 (1987).

Nimni, M., Ph.D., "The Cross-Linking and Structure Modification of the Collagen Matrix in the Design of Cardiovascular Prosthesis," Journal of Cardiac Surgery, 3: 523-533 (1988).

Nogueira, L., et al., Comparison of gelatine matrix-thrombin sealants used during laparoscopic partial nephrectomy, BJU International, 102: 1670-1674 (2008).

Non-Final Office Action for U.S. Appl. No. 14/136,578, titled: "Device for Promotion of Hemostasis and/or Wound Healing", dated Oct. 2, 2014.

Non-Final Office Action for U.S. Appl. No. 14/383,461, titled: "Pressurized Container Containing Haemostatic Paste", dated Jun. 15, 2017.

Non-Final Office Action for U.S. Appl. No. 14/516,728 dated Apr. 14, 2015 "Dry Haemostatic Composition".

Non-Final Office Action for U.S. Appl. No. 14/516,728, titled: "Dry Haemostatic Composition" dated Nov. 25, 2014.

Notice of Allowability for U.S. Appl. No. 14/895,674, titled: "Vacuum Expanded Dry Composition and Syringe for Retaining Same", dated Jun. 12, 2017.

Notice of Allowance for U.S. Appl. No. 14/136,578, titled: "Device for Promotion of Hemostasis and/or Wound Healing" dated Sep. 23, 2016.

Notice of Allowance for U.S. Appl. No. 14/516,728, titled: "Dry Haemostatic Composition" dated Nov. 27, 2015.

Notice of Allowance for U.S. Appl. No. 14/895,674, titled: "Vacuum Expanded Dry Composition and Syringe for Retaining Same", dated May 30, 2017.

Notification of Transmittal of the International Search Report and the Written Opinion of the International Searching Authority for International Application No. PCT/EP2015/080761, "Syringe for Retaining and Mixing First and Second Substances", dated Feb. 19, 2016.

Novak, D., "Embolization Materials," Interventional Radiology, pp. 295-313 (1990).

O'Neill, P., et al., "Use of Porcine Dermis as a Dural Substitute in 72 Patients," Journal of Neurosurgery, 61: 351-354 (1984).

Office Action for U.S. Appl. No. 14/136,578, titled: "Device for Promotion of Hemostasis and/or Wound Healing", dated Aug. 13, 2015.

Office Action for U.S. Appl. No. 14/895,674, titled: "Vacuum Expanded Dry Composition and Syringe for Retaining Same", dated Feb. 6, 2017.

Ofner, C.M. and Bubnis, W.A., "Chemical and Swelling Evaluations of Amino Group Crosslinking in Gelatin and Modified Gelatin Matrices," Pharma. Res., 13: 1821-1827 (1996).

Oyelese, Yinka, et al., "Postpartum Hemhorrage," Obstetrics and Gynecology Clinics of North America 34.3, 421-441 (2007).

Oz, M.C., et al., "Controlled clinical trial of a novel hemostatic agent in cardiac surgery.", Ann Thorac Surg, 69: 1376-1382 (2000).

Oz, M.C., et al., "Floseal-Matrix: New Generation Topical Hemostatic Sealant", J. Card. Surg., 18: 486-493 (2003).

Palm, S., et al., "Dural Closure with Nonpenetrating Clips Prevents Meningoneural Adhesions: An Experimental Study in Dogs," Neurosurgery, 45(4): 875-882 (1999).

Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," Acta Neurochirurgica, 139: 827-838 (1997).

Park, Y-K., et al., "Prevention of Arachnoiditis and Postoperative Tethering of the Spinal Cord with Gore-Tex Surgical Membrane: An Experimental Study with Rats," Neurosurgery, 42(4): 813-824 (1998).

Peppas, N. and Barr-Howell, B., "Characterization of the Cross-Linked Structure of Hydrogels," Ch. 2: Hydrogels in Medicine and Pharmacy, vol. I: Fundamentals, N. Peppas ed., pp. 27-56 (1986).

Peppas, N. and Brannon-Peppas, L, "Hydrogels at Critical Conditions. Part 1. Thermodynamics and Swelling Behavior," Journal of Membrane Science, 48: 281-290 (1990).

Peppas, N. and Khare, A., "Preparation, Structure and diffusional Behavior of Hydrogels in Controlled Release," Adv. Drug Delivery Reviews, 11: 1-35 (1993).

Peppas, N. and Korsmeyer, R, "Dynamically Swelling Hydrogels in Controlled Release Applications," Ch. 6: Hydrogels in Medicine and Pharmacy, vol. III: Properties and Applications, N. Peppas ed., pp. 109-135 (1987).

Peppas, N. and Lustig, S., "Solute Diffusion in Hydrophilic Network Structures," Ch. 3: Hydrogels in Medicine and Pharmacy, vol. I: Fundamentals, N. Peppas ed., pp. 57-83 (1986).

Peppas, N. and Mikos, A., "Preparation Methods and Structure of Hydrogels," Ch. 1: Hydrogels in Medicine and Pharmacy, vol. I: Fundamentals, N. Peppas ed., pp. 1-25 (1986).

Peppas, N. and Moynihan, H, "Structure and Physical Properties of Poly(2-Hydroxyethyl Methacrylate) Hydrogels," Ch. 2: Hydrogels in Medicine and Pharmacy, vol. II: Polymers, N. Peppas ed., pp. 49-64 (1987).

Peppas, N., "Hydrogels and Drug Delivery," Current Opinion in Colloid & Interface Science, 2: 531-537 (1997).

Peppas, N., "Hydrogels in Medicine and Pharmacy," Hydrogels in Medicine and Pharmacy, vol. 1. Fundamentals, CRC Press, Boca Raton, FL, 180 pages (1986).

Peppas, N., "Hydrogels in Medicine and Pharmacy," Hydrogels in Medicine and Pharmacy, vol. 2. Polymers, CRC Press, Boca Raton, FL, 172 pages (1987).

Peppas, N., "Hydrogels in Medicine and Pharmacy," Hydrogels in Medicine and Pharmacy, vol. 3. Properties and Applications, CRC Press, Boca Raton, FL, 196 pages (1987).

Peppas, N., "Hydrogels of Poly (Vinyl Alcohol) and its Copolymers," Ch. 1: Hydrogels in Medicine and Pharmacy, vol. II: Polymers, N. Peppas ed., pp. 57 pgs (1987).

Peppas, N., ed., "Other Biomedical Applications of Hydrogels," Ch. 9: Hydrogels in Medicine and Pharmacy, vol. III: Properties and Applications, pp. 177-186 (1987).

Pietrucha, K., "New Collagen Implant as Dural Substitute," Biomaterials, 12: 320-323 (1991).

Pitt, C., et al., "Biodegradable Drug Delivery Systems Based on Aliphatic Polyesters: Application to Contraceptives and Narcotic Antagonists," Controlled Release of Bioactive Materials, R. Baker, ed., (NY: Academic Press) pp. 19-43 (1980).

Porchet, F., et al., "Inhibition of Epidural Fibrosis with ADCON-L: Effect on Clinical Outcome One Year Following Reoperation for Recurrent Lumbar Radiculopathy," Neurological Research, 21: 551-560 (1999).

Product leaflet for FloSeal® Matrix Hemostatic Sealant dated Jul. 2001 (Jul. 2001).

Pschyrembel®—Klinisches Wörterbuch, 261st edition, de Gruyter (2007).

Purdy, P.D., et al., "Microfibrillar collagen model of canine cerebral infarction"; Strokes, 20(10): 1361-1367 (Oct. 1989).

Quintavalla, J., et al., "Fluorescently labeled mesenchymal stem cells (MSCs) maintain mutlilineage potential and can be detected following implantation into Particular cartilage defects.", Biomaterials, 23: 109-119 (2002).

Raftery, A., "Absorbable haemostatic materials and intraperitoneal adhesion formation."; Br. J. Surg. 67; 1980; pp. 57-58.

Ratner, B., "Hydrogel Surfaces," Ch. 4: Hydrogels in Medicine and Pharmacy, vol. I: Fundamentals, N. Peppas ed., pp. 85-94 (1986).

(56) References Cited

OTHER PUBLICATIONS

Raul, J.S., et al., "Utilisation du Polyester Urethane (NEUROPATCH) Comme Substitut Dural," Neurochirugie, 49: 83-89, English abstract only on p. 83 (2003).
Reddy, M., et al., "A Clinical Study of a Fibrinogen-Based Collagen Fleece for Dural repair in Neurosergery," Acta Neurochirurgica, 144: 265-269 (2002).
Reese, A.C., "Role of fibronectin in wound healing", Report date: Sep. 12, 1986; Annual rept. Oct. 1, 1985-Mar. 31, 1986, Final rept. Oct. 1, 1983-Mar. 31, 1986. Corporate Author: Medical Coli of Gerogia Augusta Research Institute. Brunt and Klausner, "Growth factors speed wound healing", Nature Biotechnology, 6(1): 25-30 (1988).
Reijnen, M.M.P.J., et al., "Prevention of intra-abdominal abscesses and adhesions using a hyaluronic acid solution in a rat peritonitis model." Arch Surg. 134: 997-1001 (1999).
Renkens, K., et al, "A Multicenter, Prospective, Randomized Trial Evaluating a New Hemostatic Agent for Spinal Surgery," Spine, 26(15): 1645-1650 (2001).
Riley, S., et al. "Percutaneous Liver Biopsy with Plugging of Needle Track: A Safe Method for Use in Patients with Impaired Coagulation," Lancet, p. 436 (1984).
Roda, A., et al., "Protein Microdeposition Using a Conventional Ink-Jet Printer," BioTechniques, 28(3): 492-496 (2000).
Romanelli, M., et al., "Exudate Management Made Easy", downloaded from http://www.woundsinternational.com, 6 pgs., (Jan. 29, 2010).
Rosenblatt, J., et al., "Effect of Electrostatic Forces on the Dynamic Rheological Properties of Injectable Collagen Biomaterials," Biomaterials, 13: 878-886 (1982).
Rosenblatt, J., et al., "Injectable Collagen as a pHSensitive Hydrogel," Biomaterials, 12: 985-995 (1984).
Ross, J., et al., "Association Between Peridural Scar and Recurrent Radicular Pain After Lumbar Discectomy: Magnetic Resonance Evaluation," Neurosurgery, pp. 855-863 (1996).
Rossler, B., et al., "Collagen Microparticles: Preparation and Properties," Journal of Microencapsulation, 12: 49-57 (1995).
Sakurabayashi, S., et al., "Clinical evaluation of new hemostatic agent for hemostasis from biopsy wounds in the liver."; Gastroenterological Endoscopy 30:(10) 29 pgs. (Oct. 1988).
Sanfilippo, J.S., et al., "Comparison of avitene, topical thrombin and Gelfoam as sole hemostatic agent in tuboplasties.", Fertility and Sterility, 33(3): 311-316 (1980).
San-Galli, F., et al., "Experimental Evaluation of a Collagen-Coated Vicryl Mesh as a Dural Substitute," Neurosurgery, 30: 396-401 (1992).
Santomaso, A., et al., "Powder flowability and density rations: the impact of granules packing", Chemical Engineering Science, 58: 2857-2874 (2003).
Schramm, V., et al., "Gelfoam Paste Injection for Vocal Cord Paralysis," The Laryngoscope, 88: 1268-73 (1978).
Shaffrey, C.I., et al., "Neurosurgical Applications of Fibrin Glue: Augmentation of Dural Closure in 134 Patients," Neurosurgery, 26: 207-210 (1990).
Shushan, A., et al., "Hyaluronic acid for preventing experimental postoperative intraperitoneal adhesions.", Journal of Reproductive Medicine, 39(5): 398-402 (1994).
Shuxian, M. and Zhili, C., "Clinical Observation of the Treatment of Hemoptysis by Ultrasonic Atomizing Inhalation of Thrombin", Chinese Journal of Critical Care Medicine, 16(2): 30 (1996).
Sidman, K., et al., "Biodegradable, Implantable Sustained Release Systems Based on Glutamic Acid Copolymers," Journal of Membrane Science, 7: 227-291 (1979).
Sigma-Aldrich Datasheet for "Hank's Balanced Salts," revised Apr. 2007.
Simamora, P., et al., "Controlled delivery of pilocarpine. 2. In-vivo evaluation of Gelfoam® device," International Journal of Pharmaceutics, 170(2): 209-214 (1998).
Smith, A., "New and Nonofficial Remedies: Absorbable Gelatin Sponge—Gelfoam-Upjohn," Council on Pharmacy and Chemistry, 135(14): p. 921 (1947).
Smith, K., et al., "Delayed Postoperative Tethering of the Cervical Spinal Cord," Journal of Neurosurgery, 81: 196-201 (1994).
Solar Biologicals Inc., "Solar-cult sampling products: Pre-moistened cellulose sponge sampling systems", available at www.solarbiologicals.com/samp-sys.htm (Jul. 25, 2002).
Soules, M.R., et al., "The prevention of postoperative pelvic adhesions: An animal study comparing barrier methods with Dextran 70.", Am. J. Obstet. Gynecol., 143(7): 829-834 (1982).
Spence et al., "Cerebellar capillary hemangioblastoma: its histogenesis studied by organ culture and electron microscopy.", Cancer, 35(2): 326-341 (Feb. 1975).
Spotnitz, W. D., et al., "Hemostatus, Sealants, and Adhesives: Components of the Surgical Toolbox," Transfusion, 48(7):1502-1516 (2008).
Springorum, H., "Die Verwendung von Kollagenfolien Zur Uberbruckung von Defekten des Gleitgewebes bei Achillotenotomien und Achillessehnenrupturen," Akt. Traumatol., 15: 120-121, English abstract only on p. 120 (1985).
Stief, T. W., "Kallikrein Activates Prothrombin," Clinical and Applied Thrombosis/Hemostasis, 14.1:97-98 (2008).
Stricker, A., et al., "Die Verwendung von TissuFoil Membran bei der Sinusbodenaugmentation," Ellipse, 17: 1-5 (2001). English abstract only on p. 1.
Stuart Transport medium information sheet [retrieved online on May 27, 2009].
Sugitachi, A., et al., "A Newly Devised Chemo-Embolic Agent, G.T. XIIIADM," Gan. To. Kagaku Ryoho, 12: 1942-1943 (1985). English abstract retrieved from http://www.ncbi.nlm.nih.gov on Jan. 2, 2001.
Sugitachi, A., et al., "Locoregional Therapy in Patients with Malignant Pleural Effusion—Two Different Kinds of 'BAC Therapy'," Gan. To. Kagaku Ryoho, 19: 1640-1643 (1992). English abstract retrieved from http://www.ncbi.nlm.nih.gov on Jan. 3, 2001.
Sugitachi, A., et al., "Preoperative Transcatheter Arterial Chemo-Embolization for Locally Advanced Breast Cancer: Application for New Thrombotic Materials." Japanese Journal of Surgery, 13: 456-458 (1992).
Surgiflo® Essential Prescribing Information, Hemostatic Matrix (Made from Absorbable Gelatin Sponge, U.S.P.), 1 page (2005).
Surgiflo® haemostatic matrix FlexTip, MS0009, 84 pages (2007).
Surgiflo® Prescription Information, Hemostatic Matrix, (Made from SURGIFOAM* Absorbable Gelatin Sponge U.S.P.) plus FlexTip, 2 pages (2008).
Surgiflo® product leaflet, "Surgiflo® Hemostatic Matrix Kit," 5 pages (2012).
Surgiflo® product leaflet, "Surgiflo® Hemostatic Matrix," 12 pages (2009).
Swann, D.A.,"Studies on hyaluronic acid-I. The preparation and properties of rooster comb hyaluronic acid", Biochemica et biophysica acta, 156: 17-30 (1968).
Taheri, Z., "The Use of Gelfoam Paste in Anterior Cervical Fusion," Journal of Neurosurgery, 34: 438 (1971).
Tobin, M., et al., "Plugged Liver Biopsy in Patients with Impaired Coagulation," Digestive Diseases and Science, 34: 13-15 (1989).
Tucker, H., "Absorbable Gelatin (Gelfoam) Sponge," Springfield, Illinois, Charles T. Thomas, pp. 3-125 (1965).
Van den Bosch, E., et al., "Gelatin degradation at elevated temperature", International Journal of Biological Macromolecules, 32: 129-138 (2003).
Vandelli, M.A., et al., "The effect of the crosslinking time period upon the drug release and the dynamic swelling of gelatin microspheres," Pharmazie, 46: 866-869 (1991).
Vander-Salm, T.J., et al., Abstract of "Reduction of sternal infection by application of topical vancomycin.", J. of Thoracic and Cardio-vascular Surgery, 98(4): 618-622 (1989).
Verhoeven, A.G., et al., "XV. The use of microporous polymeric powders for controlled release drug delivery systems," Controlled Drug Delivery. Ch. 15, International Symposium of the Association for Pharmaceutical Technology (APV), Bad Homburg, Nov. 12-14, 1984, pp. 226-237.

(56) References Cited

OTHER PUBLICATIONS

Vinas, F., et al., "Evaluation of Expanded Polytetrafluoroethylene (ePTFE) versus Polydioxanone (PDS) for the Repair of Dura Mater Defects," Neurological Research, 21: 262-268 (1999).
Wachol-Drewek, Z., et al., "Comparative investigation of drug delivery of collagen implants saturated in antibiotic solutions and a sponge containing gentamicin.", Biomaterials, 17: 1733-1738 (1996).
Wallace, D., "The Relative Contribution of Electrostatic Interactions to Stabilization of Collagen Fibrils," Biopolymers, 29: 1015-1026 (1990).
Wallace, D., et al., "Injectable Cross-Linked Collagen with Improved Flow Properties," Journal of Biomedical Materials Research, 23: 931-945 (1989).
Warren, W., et al., "Dural Repair Using Acellular Human Dermis: Experience with 200 Cases: Technique Assessment," Neurosurgery, 46: 1391-1396 (2000).
Wassersug, J.D., M.D., "Use of Human Thrombin in Some Cases of Pulmonary Hemorrhage" Pulmonary Hemorrhage, vol. XVII, pp. 354-356 (Mar. 1950).
Weeks, R., "Microscopy of Soft Materials," Chapter 1 in Experimental and Computational Techniques in Soft Condensed Matter Physics, Jeffrey Olafsen, Ed, 2010 (2010).
West et al., "Efficacy of adhesion barriers: Resorbable hydrogel, oxidized regenerated cellulose and hyaluronic acid.", The Journal of Reproductive Medicine, 41(3) 149-154 (1996).
Wiesenthal, A.A., et al., Abstract of "New method for packing the external auditory canal, middle ear space, and mastoid cavities after otologic surgery", The Journal of Otolaryngology; 28(5): 260-265 (1999).
Wilkinson, H., et al., "Gelfoam Paste in Experimental Laminectomy and Cranial Trephination," Journal of Neurosurgery, 54: 664-667 (1981).
Written Opinion for International Application No. PCT/DK2003/000855, "Gelatine-Based Materials as Swabs", dated Feb. 28, 2005.
Written Opinion of counterpart International Preliminary Examining Authority for counterpart International Application No. PCT/DK2011/050082, "A Method for Promotion of Hemostasis and/or Wound Healing", dated Mar. 23, 2012.
Written Opinion of the International Searching Authority (Corrected Version) for International Application No. PCT/DK2005/000063, "Haemostatic Sprays and Compositions".
Written Opinion of the International Searching Authority for International Application No. PCT/DK2005/000475, "Haemostatic Composition Comprising Hyaluronic Acid".
Written Opinion of the International Searching Authority for International Application No. PCT/DK2009/050048, "Device for Promotion of Hemostatis and/or Wound Healing", completed Aug. 31, 2010.
Wu, Y. et al., Abstract of "Design and experimental study of a slow-release antibiotic membrane implant in surgery wound.", Intern. Des Services de San. Des Forces Armees; 72(7-9): 194-196 (Sep. 1999).
Xing, Q., et al., "Increasing Mechanical Strength of Gelatin Hydrogels by Divalent Metal Ion Removal", Sci. Rep., 4: 4706: DOI:10.1038/srep04706(2014).
Xu, T., et al., "Viability and electrophysiology of neural cell structures generated by the inkjet printing method", Biomaterials, 27: 3580-3588 (2006).
Xu, T., et al., "Inkjet Printing of Viable Mammalian Cells," Biomaterials, 26: 93-99 (2005).
Yaping, G., "Observation and Nursing of the Treatment of Hemoptysis of Pulmonary Tuberculosis by Ultrasonic Atomizing Inhalation of Thrombin", Journal of Qilu Nursing, 10(2): 126 (Feb. 2004).
Youwen, W. et al., "Clinical Observation of the Therapeutic Efficacy of the Treatment of 15 Patients with Hemoptysis by Ultrasonic Atomizing Inhalation of Thrombin", Chengdu Medical Journal, 30(5): 262 (Oct. 2004).
Yuki, N., et al., "Effects of Endoscopic Variceal Sclerotherapy Using GT XIII on Blood Coagulation Tests and the Renal Kallikrein-Kinin System," Gastroentral. Japan, 25: 561-567 (1990). English abstract retrieved from http://www.ncbi.nlm.nih.gov [retrieved on Jan. 2, 2001].
Ziegelaar, B., et al., "The Characterisation of Human Respiratory Epithelial Cells Cultured on Resorbable Scaffords: First Steps Towards a Tissue Engineered Tracheal Replacement," Biomaterials, 23: 1425-1438 (2002).
Ziegelaar, B., et al., "Tissue Engineering of a Tracheal Equivalent, Doctoral Thesis," Munich, Germany, Ludwig Maximilians University, 2004, 25 pages (2004).
Zins, M., et al., "US-Guided Percutaneous Liver Biopsy with Plugging of the Needle Track: A Prospective Study in 72 High-Risk Patients," Radiology, 184: 841-843 (1992).
Notice of Allowance for U.S. Appl. No. 14/980,254, titled: "Dry Haemostatic Composition", dated Jan. 24, 2018.
Notification of Transmittal of the International Search Report and the Written Opinion of the International Searching Authority for International Application No. PCT/EP2016/065260, "Syringe for Mixing Two Components and for Retaining a Vacuum in a Storage Condition", dated Oct. 4, 2016.
International Preliminary Report on Patentability for International Application No. PCT/EP2016/065260, "Syringe for Mixing Two Components and for Retaining a Vacuum in a Storage Condition", date of completion Dec. 6, 2017.
Notice of Allowability for U.S. Appl. No. 14/980,254, titled: "Dry Haemostatic Composition", dated Feb. 13, 2018.
Office Action for U.S. Appl. No. 15/102,994, titled: "Dry Composition Comprising an Extrusion Enhancer", dated Feb. 22, 2018.
Notice of Allowance for U.S. Appl. No. 15/102,994, titled: "Dry Composition Comprising an Extrusion Enhancer", dated Jun. 25, 2018.
Office Action for U.S. Appl. No. 15/580,181, titled: "Syringe for Mixing Two Components and for Retaining a Vacuum in a Storage Condition", dated Aug. 23, 2019.

* cited by examiner

SYRINGE FOR RETAINING AND MIXING FIRST AND SECOND SUBSTANCES

This application is the U.S. National Stage of International Application No. PCT/EP2015/080761, filed Dec. 21, 2015, which designates the U.S., published in English, and claims priority under 35 U.S.C. §§ 119 or 365(c) to EP Application No. 14200323.5, filed Dec. 24, 2014. The entire teachings of the above applications are incorporated herein by reference.

FIELD OF INVENTION

The present disclosure relates to a syringe for mixing two substances which have been retained separately inside the syringe. In particular the present disclosure relates to a syringe for 1) retaining a dry composition in a vacuum, and 2) mixing the dry composition with an aqueous medium to form a flowable substance.

BACKGROUND OF INVENTION

Mixing procedures and manipulations of different substances can be time consuming. In an Operation Room (OR) setting this time consumption may be critical when using a haemostatic paste for inhibiting bleedings as the surgeon will have to interrupt his procedure while waiting for the haemostat. Mixing substances from different containers may also potentially compromise the sterility of the haemostatic paste and can negatively affect the consistency of the haemostatic paste. A correct paste consistency is important for a satisfactory haemostatic effect.

Conventional haemostatic pastes are prepared at the point of use by mechanical agitation and mixing of loose powder and liquid to provide uniformity of the composition. Only after the paste is formed may the paste be placed into a delivery means or applicator, e.g. a syringe, and applied to the wound.

This procedure has been improved by for example Floseal® Haemostatic Matrix (Baxter) and Surgiflo® Haemostatic Matrix (Ethicon) where one syringe (Syringe I) is preloaded with loose gelatine powder or a pre-wetted paste, and a second syringe (Syringe II) with liquid. When it is time to make a paste, Syringes I and II are connected via a luer lock and the solution in Syringe II is pushed into Syringe I. By attempting to pass the solution and powder repeatedly back and forth between Syringes I and II, a homogeneous paste is eventually formed.

Pending PCT application WO 2014/202760 filed 20 Jun. 2014 and entitled "Vacuum expanded dry composition and syringe for retaining same" relates to a method for vacuum expansion of a paste prior to freeze-drying said paste to achieve a dry composition, which upon addition of an adequate amount of an aqueous medium, reliably and consistently reconstitutes to form a substantially homogenous and flowable paste within seconds, thereby eliminating the need for undesirable mixing requirements. This application further discloses a syringe for retaining the dry composition in a vacuum and forming the paste in the syringe after addition of the aqueous medium from an external liquid receptacle.

SUMMARY OF INVENTION

The present disclosure relates to a syringe for retaining and/or mixing first and second substances comprising a barrel comprising a vacuum chamber for holding a first substance, a plunger incorporating a reservoir chamber for holding a second substance and configured to be axially displaced in the vacuum chamber, and a valve for controlling and/or establishing a fluid connection between the vacuum chamber and the reservoir chamber.

The syringe may advantageously be configured such that in a first configuration the first substance can be retained under vacuum in the vacuum chamber. The vacuum retaining first configuration may then be a storage condition of the syringe. For example the syringe is configured such that the syringe can be stored in the storage condition, i.e without losing the vacuum in the vacuum chamber, for an extended period of time, such as at least 1 month, or at least 3 or 6 months, preferably at least 1 year, more preferably at least 2 years.

Hence, the presently disclosed syringe is preferably configured such that a vacuum can be generated and retained in the vacuum chamber. Generation of the vacuum in the vacuum chamber is typically provided by an external vacuum generating means, such as a pump. As also explained in further detail below the syringe may for example be provided with structural elements that makes it possible to generate the vacuum in one configuration of the syringe, i.e. by means of having vacuum bypass channels in the barrel. The vacuum generated in this configuration can then be retained in the first configuration of the syringe.

In the vacuum retaining first configuration the vacuum chamber is a closed container. Such a configuration may be useful not only to store the substance in the vacuum chamber, but can also be considered a "charged" state of the syringe in that there is in an inherent energy in the vacuum chamber. Hence, in the first configuration the syringe can be said to be in a state with an inherent potential energy that can later be used to mix the substances of the two chambers, preferably without adding any external manual force, e.g. to move the plunger. This potential energy can be converted to an aspiration force. Therefore, if the syringe is configured to retain vacuum in the vacuum chamber in a first configuration, this force could then be at least partly utilized to fluidly connect the vacuum chamber and the reservoir chamber and bring the two substances together. Advantageously the aspiration force may be at least partly utilized on the plunger, for example used to draw the plunger towards the distal end of the syringe. The aspiration force may also be at least partly utilized to engage the valve to establish a fluid connection between the vacuum chamber and the reservoir chamber. If at least a part of the vacuum is still present in the vacuum chamber a pressure difference exists between the vacuum chamber and the reservoir chamber, and an aspiration force arises that can draw the second substance in the reservoir chamber into the vacuum chamber such that the two substances can mix in the vacuum chamber.

Hence, in the preferred embodiment of the presently disclosed syringe a second configuration is provided in which the valve provides a fluid passageway between the reservoir chamber and the vacuum chamber.

A major advantage of the presently disclosed syringe is therefore that first and second substances can be retained and stored within the syringe. The substances may be easily mixed within the syringe when needed without connecting external receptacle and without using external mixing containers. The presently disclosed syringe can therefore be used for many purposes where first and second substances are advantageously retained separately (e.g. for storage) and for subsequent mixing and delivery when needed.

One advantage of the presently disclosed syringe is that a reservoir chamber is incorporated in the plunger for holding the second substance, i.e. the plunger in itself defines a reservoir chamber, e.g. by provision of a hollow plunger, such as a cylindrical plunger, such that the reservoir chamber to the sides are defined by side walls of the plunger. Using the space inside the plunger to store one of the components makes the syringe more compact and lighter. The fact that the plunger is the movable part of the syringe (in relation to the barrel) can also render the design simple in that it is possible to mount the valve on the distal part of the plunger.

Another advantage of the presently disclosed syringe is the vacuum chamber in the barrel for holding a first substance. If vacuum is created in the vacuum chamber, the vacuum may be utilized to move the plunger towards the vacuum chamber and to aspirate the second substance from the reservoir chamber to the vacuum chamber. By first applying vacuum in the vacuum chamber and then letting the vacuum pull the plunger and mix the substances, the mixing process can be provided in a very controlled manner without involving manual force or manual movement of the plunger. If the parts of the plunger are produced in a process in which the parts always have the same size and shape, for example by injection moulding, and the vacuum generation is applied in the same way, it can also be expected that the mixing will be performed in the same way every time.

The valve may be attached to the plunger which is axially slidable in relation to the barrel. The valve may thereby constitute a separating barrier between the two chambers. As the vacuum in the vacuum chamber may be used to distally move the plunger in the barrel, the valve may be engaged by this distal plunger movement to establish a fluid connection between the two chambers.

The combination of several of the abovementioned features can also be considered to further improve the design, which can be used with a range of additional mechanisms in order to make use of the invention. For example, the syringe may further comprise different kind of locking members to control the axial positions of the plunger inside the barrel. If vacuum is applied inside the vacuum chamber a mechanical locking mechanism can ensure that the plunger is not moved towards the vacuum chamber until the user removes the lock.

However, in particular the method disclosed in WO 2014/202760, for vacuum expansion of a paste prior to freeze-drying said paste to achieve a dry composition which reconstitutes efficiently to form a flowable paste upon addition of an aqueous medium, can be efficiently realized by means of the presently disclosed syringe.

Furthermore, the method disclosed in WO 2014/202760 for preparing a dry composition, which reconstitutes spontaneously within seconds to a ready-to-use paste suitable for haemostatic and/or wound healing purposes can also be efficiently realized by means of the presently disclosed syringe.

The expanded dried paste disclosed in WO 2014/202760 reconstitutes efficiently upon addition of a liquid. The paste may form independently of external stimuli, such as mixing or stirring of any kind. The dry composition disclosed in WO 2014/202760 may reconstitute spontaneously upon addition of a liquid, i.e. no mechanical mixing is required for a paste to form. Upon addition of a suitable amount of an aqueous medium, a ready-to-use paste suitable for use in haemostasis and/or wound healing forms spontaneously within seconds. Vacuum freeze-drying and vacuum storage of the dry composition may be provided by means of the herein disclosed syringe. Furthermore, retaining and storage of the aqueous medium and mixing with the aqueous medium, subsequent reconstitution in the vacuum chamber and controlled release of the ready-to-use paste may also be provided by means of the herein disclosed syringe. This paste disclosed in WO 2014/202760 is superior to the currently available flowable products as it reduces or obviates the need for mechanical mixing steps. That no mechanical mixing is required also means that the variation in paste consistency is minimised and less time is spent preparing the paste, which in turn leads to increased patient safety, both due to the fact that the haemostatic paste can be applied to the patient faster and that the simple preparation method decreases the likelihood of mistakes being made during the preparation of the haemostatic paste. Hence, a flowable paste can be extruded from the presently disclosed syringe and applied to a patient, e.g. to a bleeding wound, within seconds of unlocking the syringe, because the mixing of the substances can be provided automatically.

Hence, in one embodiment the presently disclosed syringe comprises a dry composition in the vacuum chamber. The pressure within the vacuum chamber is advantageously less than the pressure outside the vacuum chamber, e.g. the dry composition may be retained in a vacuum. The dry composition may be obtained as described in WO 2014/202760, hence the dry composition may be in the form of a vacuum expanded, freeze-dried paste, preferably with a density of the freeze-dried paste of between about 1 mg/ml to about 40 mg/ml, such as between about 5 mg/ml to about 35 mg/ml, for example between about 10 mg/ml to about 35 mg/ml. The dry composition may be capable of forming a paste upon addition of an aqueous medium as also described in WO 2014/202760. The aqueous medium is preferably retained in the reservoir chamber of the presently disclosed syringe.

The presently disclosed syringe may be suitable for many applications, for example for mixing a drug with an infusion substance or for mixing two drugs, but in particular for lyophilized drugs. These are normally stored in vials and need reconstitution prior to administration, typically by mixing with some sort of infusion substance. Subsequently the reconstituted drug is used for its medical purpose. With the presently disclosed syringe the lyophilized drug can be retained in vacuum in the syringe together with the infusion substance in the correct mixing ratio under sterile conditions. The reconstituted drug can subsequently be injected from the syringe directly into an infusion bag. This can lead to increased patient safety and improved drug handling capability in many applications.

The first and second substances retained by means of the presently disclosed syringe are preferably sterile. The syringe may also be sterile. Any suitable sterilisation technique known in the art may be utilised. The sterilisation may occur after the packaging step, i.e. when the syringe is contained within an outer packaging. Thus, in a preferred embodiment sterilisation is terminal sterilisation.

Figure 1A:
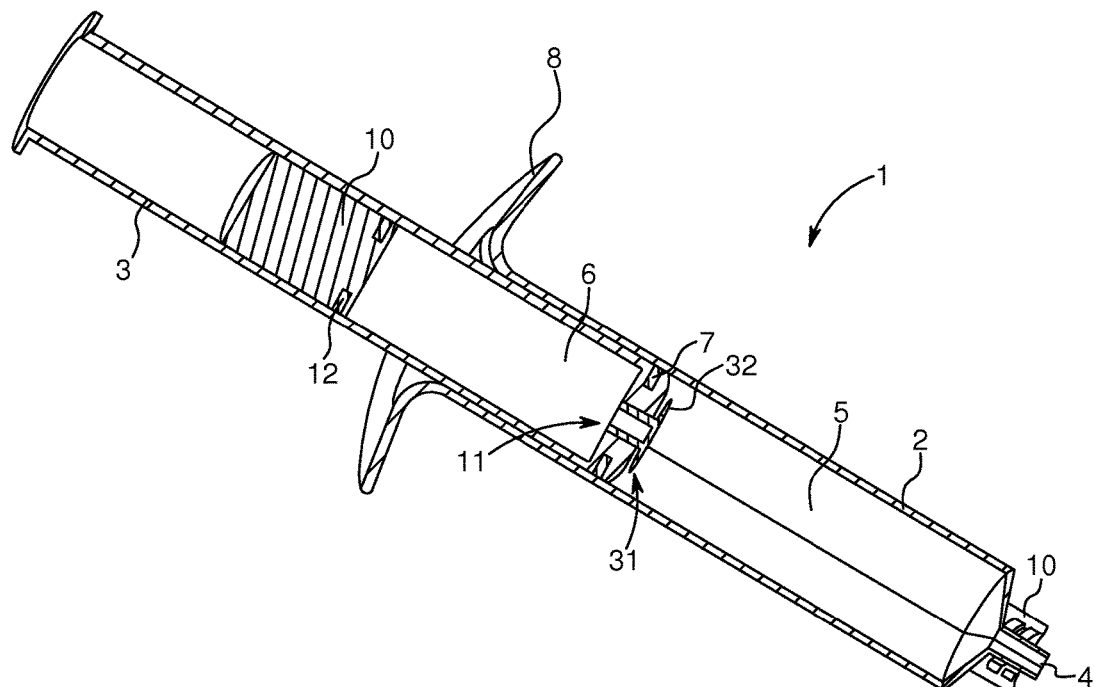
FIG. 1A shows a cross-sectional illustration of one embodiment of the presently disclosed syringe with empty vacuum and reservoir chambers.

The drawings are exemplary only and should not be construed as limiting the scope of the invention.

Definitions

"Ambient pressure" is herein used interchangeably with the term "atmospheric pressure". It is the pressure in the surrounding area, i.e. the pressure in the location in which a process takes place.

A "reduced pressure" is a pressure below ambient pressure, i.e. a pressure below that of the pressure in the surrounding area in which a certain process operates.

A "paste" according to the present disclosure has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes paste to demonstrate properties of fragile matter. A paste is not a gel/jelly. A "slurry" is a fluid mixture of a powdered/pulverized solid with a liquid (usually water). Slurries behave in some ways like thick fluids, flowing under gravity and being capable of being pumped if not too thick. A slurry may be regarded as a thin paste, i.e. a slurry generally contains more water than a paste. A paste has pores comprising expandable gas or air.

The term "spontaneous" is used to describe phenomena arising from internal forces or causes, which are independent of external agencies or stimuli and which happen within a short period of time, i.e. preferably within less than about 30 seconds, more preferred within less than about 20 seconds, even more preferred within less than about 10 seconds or within less than about 5 seconds, such as within less than about 3 seconds, for example less than about 2 seconds.

"Vacuum" is herein defined as a region with a gaseous pressure less than the ambient pressure, i.e. the surrounding atmospheric pressure. At sea level on Earth the atmospheric pressure is approximately 1 bar, i.e. 1000 mbar at 25° C. The below table shows the approximate pressures in "low", "medium" and "high" vacuum at sea level on earth in millibar (mbar).

|  | pressure (mbar) |
| --- | --- |
| Atmospheric pressure | 1000 |
| Low vacuum | 1000 to 100 |
| Medium vacuum | 100 to 0.001 |
| High vacuum | <0.001 |

DETAILED DESCRIPTION OF THE INVENTION

As stated previously one embodiment of the present disclosure relates to a syringe for retaining and/or mixing first and second substances comprising a barrel comprising a vacuum chamber for holding a first substance, a plunger incorporating a reservoir chamber for holding a second substance and configured to be axially displaced in the vacuum chamber, and a valve for controlling and/or establishing a fluid connection between the vacuum chamber and the reservoir chamber. The syringe may then advantageously be configured such that in a first (syringe) configuration the first substance can be retained under vacuum in the vacuum chamber, and in a second (syringe) configuration the valve provides a fluid passageway between the reservoir chamber and the vacuum chamber. The first configuration may be a locked configuration. Further, the reservoir chamber and the vacuum chamber may be fluidly disconnected in said first configuration. The first configuration may also be characterized in that a potential mechanical energy is stored in the syringe in said first configuration. This potential mechanical energy may, upon changing the configuration of the syringe, be converted to kinetic energy that can be used to create a fluid connection between the reservoir chamber and the vacuum chamber such that two substances can be mixed. Hence, upon changing the configuration of the syringe from the first configuration no external forces are required to mix the substances—the potential energy stored in the vacuum in the vacuum chamber in the syringe in the first configuration is in amount that is sufficient to provide the mixing. Hence, a self-mixing syringe is provided by the presently disclosed syringe.

The first configuration of the syringe may therefore be compared with a spring which is locked in a stretched configuration. The forces created by a vacuum retained in the vacuum chamber can in one embodiment be compared to a situation where one end of a stretched spring is connected to the distal end of the inside of the barrel and the other end of the spring is connected to the distal end of the plunger which is inside the barrel as well. The locked stretched spring stores potential mechanical energy and when unlocked and released the spring will draw the plunger in the distal direction inside the barrel.

Hence, in one embodiment a first configuration of the syringe corresponds to a first locked axial position of the plunger inside the barrel, wherein the first substance can be retained under vacuum in the vacuum chamber, and in a second configuration the plunger is unlocked and the vacuum in the vacuum chamber draws the plunger in a distal axial direction such that the valve is engaged to provide a fluid passageway between the reservoir chamber and the vacuum chamber.

In the preferred embodiment the vacuum chamber is defined inside the barrel; distally by the distal end of the barrel and proximally by the distal end of the plunger. The valve may be located in the distal end of the plunger thereby providing separation between the vacuum chamber inside the barrel and the reservoir chamber inside the plunger.

Correspondingly, the reservoir chamber and the vacuum chamber may be fluidly connected in said second configuration. E.g. upon user interaction the lock can be removed and the syringe is then advantageously configured such that the second configuration is automatically attained. This may be provided by exploiting the lowered pressure that can be retained in the vacuum chamber, e.g. a vacuum in the vacuum chamber can suck the plunger towards the distal end of the plunger. The syringe may then be configured such that this distal plunger movement opens the valve to establish a fluid connection between the reservoir chamber and the vacuum chamber. A liquid stored in the reservoir chamber may then be sucked into the vacuum chamber, again due to the lower pressure in the vacuum chamber if a vacuum is retained therein.

In the case of vacuum expanded paste as disclosed in WO 2014/202760 used in connection with the syringe as herein disclosed the freeze dried composition and the liquid then mixes in the vacuum to become a ready-to-use flowable paste in a few seconds and can be delivered from the vacuum chamber, e.g. through an outlet in the distal end of the barrel by manually controlling the plunger. E.g. upon unlocking the syringe from the first configuration a ready-to-use flowable paste can be provided automatically in a few seconds in a closed sterilized environment without human intervention and without breaking any sterilized borders.

In the preferred embodiment the barrel comprises an open proximal end. The proximal end of the plunger may then extend through the open proximal end of the barrel. The syringe is then preferably configured such that the plunger can be axially displaced through the open proximal end of the barrel. The syringe preferably comprises a sealed engagement between the plunger and barrel, e.g. in the form of a rubber seal in a distal end of the plunger as illustrated in FIGS. 1A, 2 and 4. The open proximal barrel end and the plunger extending through it as illustrated in FIGS. 1 and 2 is a standard solution for a syringe The syringe may be prefilled with the first and second substances and the syringe is preferably configured such that the first and second substances can be stored and retained as part of the syringe. The first substance may be any substance and composition, but it may in particular be a solid, such as a dry composition, such as a freeze dried paste or drug, such as a vacuum expanded freeze dried paste or drug. The second substance may be any substance and composition, but it may in particular be a fluid, such as a liquid, such as water.

Figure 2A:
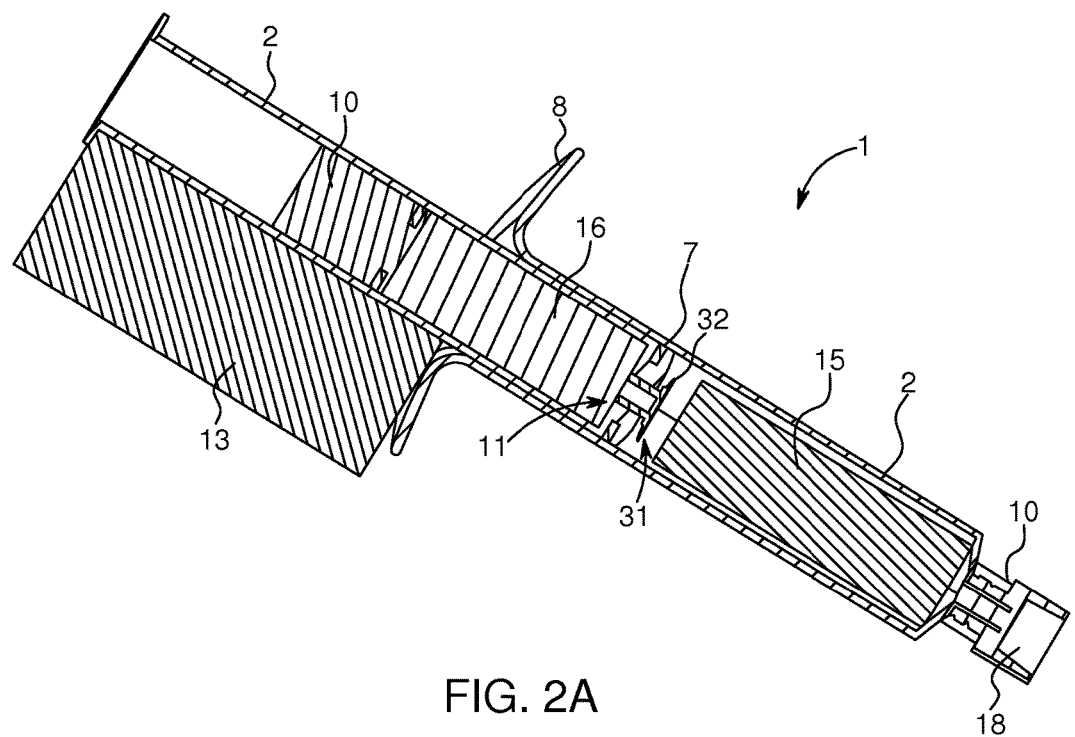
FIG. 2A shows a cross-sectional illustration of the syringe in FIG. 1A in a locked configuration with a first substance in the vacuum chamber and a second substance in the reservoir chamber.
Figure 2B:
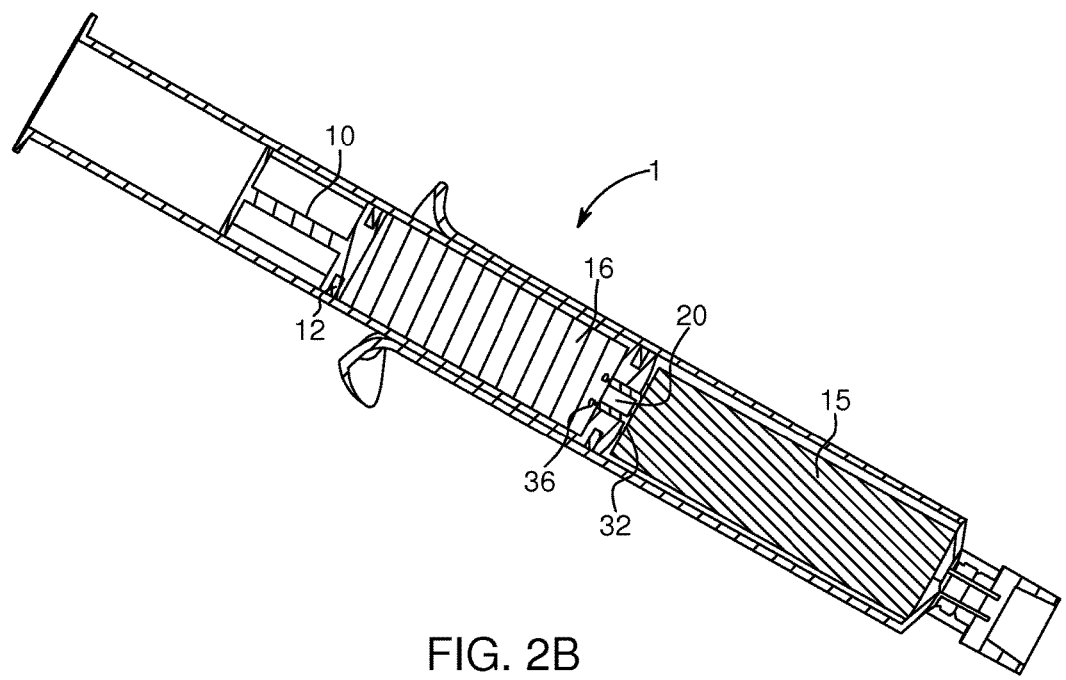
FIG. 2B shows a cross-sectional illustration of the syringe in FIG. 2A when the locking element has been removed and the valve is open.

The barrel comprises an outlet for disposing the mixed final product. This outlet is preferably closable and/or sealable in order to retain the vacuum in the vacuum chamber. The outlet may e.g. be a Luer type outlet and it is advantageously located at the distal end of the barrel. The outlet may further be formed as a connector portion suitable for connecting with another mating connector, e.g. suitable for connecting a hose to the syringe as also illustrated in FIGS. 1A and 2A. The connector portion may be a connector portion of a standard type, such as a Luer lock or Luer slip connector, preferably a male Luer lock or Luer slip connector. The connector portion may be provided with a threaded portion for secure connection with matching connector. This threaded portion may be provided at the inside of the connector portion as illustrated in FIGS. 1A, 2A and 2B.

By incorporating the plunger in the reservoir chamber, the syringe can be made more compact and lighter compared to a solution in which the barrel contains two chambers for separates substances. In one embodiment the reservoir chamber is completely contained in the plunger, and/or wherein the reservoir chamber is at least partly defined by outer walls of the plunger. Preferably the reservoir chamber is a closed volume within the walls of the plunger, possible having a lid or cap, alternatively having a plug inside the hollow plunger. In one embodiment the reservoir chamber is defined by a hollow portion of the plunger.

In the preferred embodiment of the presently disclosed syringe the plunger is hollow in order to accommodate the reservoir chamber, i.e. the plunger may comprise a hollow body, i.e. a liquid reservoir may be incorporated in a hollow body of the plunger. Hence, the reservoir chamber is preferably defined by a hollow portion of the plunger. Further, the reservoir chamber is most practically located in the distal part of the plunger, i.e. closest to the vacuum chamber. The syringe may further comprise a plug, e.g. in the form of a piston, inside the hollow plunger. The plug is preferably sealably engaged with the inside surface of the hollow plunger, wherein the reservoir chamber is defined (proximally) by the plug inside the hollow plunger. The position of the plug thus defines the volume of the reservoir chamber. Further, the plug is preferably configured to be axially displaced within the hollow body of the plunger. Preferably the plug is completely contained within the hollow body of the plunger, e.g. the plug may be recessed within the hollow body of the plunger as also illustrated in FIGS. 1A and 2A, where it is seen that the plug can be formed as a small plunger or piston adapted to fit and be recessed within the hollow plunger. Incorporating the reservoir chamber and the plug completely within the plunger can make the plug and the reservoir chamber inaccessible from outside the syringe. The plug may then advantageously be configured to be axially displaced distally within the hollow body of the plunger during discharge/flushing of the second substance in the reservoir chamber into the vacuum chamber. If a vacuum is present in the vacuum and the valve establishes a fluid connection between the reservoir chamber and the vacuum chamber any fluid content in the reservoir chamber will consequently be sucked into the vacuum chamber, i.e. a second substance in the reservoir chamber will be discharged/flushed into the vacuum chamber. The vacuum may further draw the plug such that the plug is axially and distally displaced during discharge of the reservoir thereby functioning as a vacuum operated plunger or piston. Thus, the reservoir chamber can be discharged, emptied and minimized and the substances consequently mixed without direct human intervention.

In one embodiment the syringe is configured such that the suction of the second substance, located in the reservoir chamber, into the vacuum chamber (caused by the vacuum) draws the plug inside the plunger distally towards the distal end of the plunger thereby gradually minimizing the volume of the reservoir chamber. When the plug reaches the distal end of the inside of the plunger, the volume of the reservoir chamber is essentially 0. The plug and the valve may then advantageously be configured such that this distal movement of the plug causes the valve to change from an open position and back to the closed position when the reservoir chamber is emptied. Hence, the presently disclosed syringe may be configured such that upon discharge of the second substance in the reservoir chamber into the vacuum chamber the valve is engaged from the open valve configuration into the closed valve configuration thereby blocking the fluid passageway between the reservoir chamber and the vacuum chamber. This may be considered to be a third configuration of the syringe where the mixed substance is ready for ejection through the outlet of the syringe by means of operating the plunger. Re-closing of the valve helps to avoid that the mixed substance in the vacuum chamber moves proximally into the reservoir chamber during discharge of the mixed substance from the syringe.

In one embodiment of the presently disclosed syringe the first configuration corresponds to a first axial position of the plunger in the barrel. The second configuration may similarly correspond to at least a second axial position of the plunger in the barrel. The syringe may be configured such that the plunger is locked in the first configuration, e.g. the plunger may be restricted from axial displacement in said first configuration, such as that the plunger is restricted from axial displacement in a distal direction in said first configuration. Locking of the plunger may for example be provided by means of a removable locking element for locking the plunger in said first configuration. The locking element may be adapted to be removably attached to a part of the plunger extending from the proximal end of the barrel as exemplary illustrated in FIGS. 1B and 2A. In the case of a vacuum in the vacuum chamber the plunger in the barrel will be drawn towards the distal end. The locking element is advantageously configured to restrict the plunger from this distal movement. I.e. the locking element is restricting the plunger from a distal axial movement whereas the vacuum will be restricting the plunger from a proximal axial movement whereby the plunger is locked. The locking element may be configured to be snap fitted to the plunger, i.e. it is tightly attached to the plunger but may be removed relatively easily by human intervention. Once the locking element is removed the plunger will be sucked into the barrel if a vacuum is present in the vacuum chamber.

The valve is advantageously located in the distal end of the plunger. Furthermore, the valve may be configured to have a closed valve configuration disconnecting the reservoir chamber and the vacuum chamber and an open valve configuration fluidly connecting the reservoir chamber and the vacuum chamber. This may for example be provided if the valve comprises at least one axially displaceable element. The open valve configuration may then correspond to a first position of said axially displaceable element and wherein the closed valve configuration corresponds to a second position of said axially displaceable element. The valve may further be configured such that said axially displaceable element protrudes into the vacuum chamber in said first position. The valve may further be configured such that the axially displaceable element protrudes into the reservoir chamber in said second position. The valve and the axially displaceable element may further be configured such that in the open configuration of the valve the axially displaceable element protrudes into the reservoir chamber and into the vacuum chamber.

An exemplary form of the axially displaceable valve element is illustrated in FIG. 3. The axially displaceable element preferably comprises one or more fluid bypass channels providing the fluid connection between the reservoir chamber and the vacuum chamber in the open configuration of the valve. These channels may be located externally on the side of the displaceable element as illustrated in FIG. 3. At a distal end the axially displaceable valve element may comprise a plane closed surface extending into the vacuum chamber, said plane surface defining a plane substantially perpendicular to the longitudinal axis of the syringe. The axially displaceable element may thus be formed like a plunger. Furthermore, the axially displaceable element may be rotatably locked in the valve. The plane surface provides and enlarged contact area compared to the cross-sectional area of the remaining part of the valve part. This contact area is provided to establish contact with a first substance inside the vacuum chamber. The axially displaceable valve part may be protruding into the vacuum chamber in the closed configuration of the valve. During a distal axial movement of the plunger in the barrel this enlarged contact area may eventually come into contact with a first substance in the vacuum chamber. This contact may then cause the valve part to be displaced axially in the proximal direction converting the valve into the open configuration establishing a fluid connection between the reservoir chamber and the vacuum chamber. Correspondingly the valve may be converted back into the closed position when the reservoir chamber is empty. This may be provided with the plug inside the plunger as illustrated in the drawings. When the plug reaches the distal end of the inside of the plunger it may engage the axially displaceable element and displace it distally to convert the valve back into the closed position.

The axially displaceable element exemplified in FIG. 3 is preferably fully or partly manufactured in rubber or a soft rubber like material, such as silicone or an elastomer, i.e. such that the element is substantially soft and elastic. This is to provide a better sealed closing of the valve.

As previously indicated the syringe may be configured such that upon unlocking the plunger, a vacuum in the vacuum chamber may cause an axial displacement of the plunger from a first position to a second position. This axial displacement of the plunger from a first position to a second position may engage the valve to establish a fluid passageway between the reservoir chamber and the vacuum chamber. E.g. the syringe may be configured such that a first substance, preferably in the form of a solid, located in the vacuum chamber engages the valve upon contact between valve and solid during axial displacement of the plunger towards the distal end of the barrel, to establish a fluid passageway between the reservoir chamber and the vacuum chamber.

Prior to freeze-drying of e.g. a paste in a vacuum chamber the vacuum that can be created is important to expand the paste in order to increase the surface area and expedite the following freeze drying. By retaining the freeze-dried paste in a vacuum in the vacuum chamber of the syringe after the freeze drying process is finished, i.e. at a pressure level lower than surrounding ambient pressure, addition of liquid upon preparation and use of the paste is eased, because the liquid is sucked into the vacuum chamber due to the reduced pressure in the vacuum chamber.

Opening the valve as a result of unlocking the plunger/syringe and/or a distal movement of the plunger may be solved by other embodiment of the valve and/or the axially displaceable part. E.g. a small protrusion at the inner surface of the vacuum chamber may activate the valve when a certain part of the plunger or the valve engages or passes this protrusion. Thereby the valve is engaged by other means than by contact with a substance in the vacuum chamber.

Figure 1B:
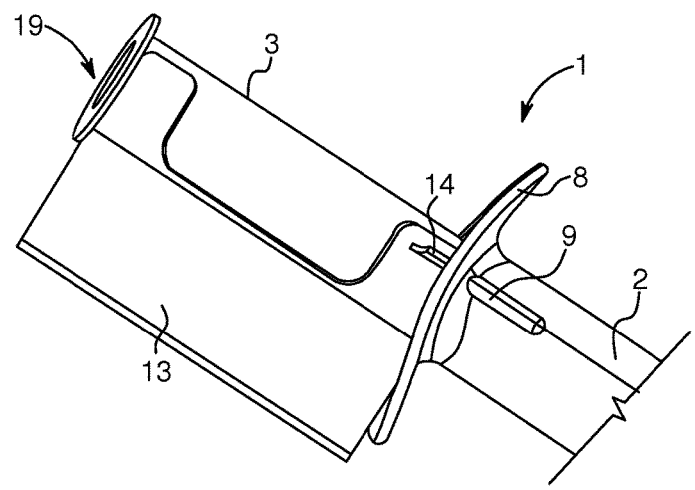
FIG. 1B shows the proximal end of one embodiment of the presently disclosed syringe with a locking element engaging the plunger.

In one embodiment the presently disclosed syringe further comprises one or more vacuum bypass channels, preferably located in the barrel and/or in the plunger. The vacuum bypass channel, aka lyophilisation bypass channel, being a gaseous communication between the vacuum chamber of the syringe and the outside of the barrel, i.e. the external environment. Vacuum bypass channels provides the advantage that a substance can be freeze-dried inside the syringe. The bypass may allow for an open state allowing for gaseous communication between the vacuum chamber and the outside, and a closed state wherein the vacuum can be retained. The bypass may be located anywhere allowing for gaseous communication between the vacuum chamber and the external environment e.g. in the barrel as shown in FIG. 1B or in the plunger. The syringe may consequently be configured such that the plunger sealably engages the vacuum chamber in at least a first axial position of the plunger inside the vacuum chamber, i.e. the state where a vacuum is retained, and such that a fluid communication is established across the plunger in at least a second axial position of the plunger inside the vacuum chamber via said one or more vacuum bypass channels, i.e. the state where a substance in the vacuum chamber can be freeze-dried during establishment of a vacuum, e.g. via suction through the bypass channel(s). Thus, the vacuum bypass channel(s) may be configured to break the sealing between the vacuum chamber and the plunger at a predefined axial position of the plunger inside the vacuum chamber. This may for example be provided if said one or more vacuum bypass channels are one or more longitudinal grooves formed in the inner surface of the proximal end of the vacuum chamber as illustrated in FIG. 1B. Alternatively the one or more vacuum bypass channels may be formed in the plunger.

Alternatively said one or more vacuum bypass channels are configured such that a fluid communication can be provided directly between the vacuum chamber and the ambient atmosphere independent of the position of the plunger, e.g. via a pressure valve located directly at the vacuum chamber.

The volume capacity presently disclosed syringe is scalable by shaping and scaling the barrel and the plunger. The volume of the vacuum chamber and the reservoir chamber can then be selected within the limits of the barrel and the plunger. The volume of the barrel and/or the volume of the vacuum chamber may be between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.

Correspondingly the volume of the hollow body of the plunger and/or the volume of the reservoir chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.

The presently disclosed syringe is preferably a single-use disposable syringe. The different components of the syringe (barrel, plunger, plug, valve, valve part, etc.) are preferably suitable for manufacture by means of single cycle injection molding.

The barrel may be provided with a flange at the proximal end of the vacuum chamber in order to ease handling of the syringe when operating the plunger as illustrated in FIGS. 1 and 2. Furthermore, the inside volume of the vacuum chamber and/or the reservoir chamber may advantageously be cylindrical.

EXAMPLES

One embodiment of the presently disclosed syringe 1 is exemplified in FIGS. 1-4. The barrel 2 is provided with a vacuum chamber 5, an outlet 4, a connector portion 10 and a flange 8 formed in a single piece and suitable for manufacture by single cycle injection moulding. A plunger 3 having a hollow body 19 extends from the open proximal end of the barrel 2. A sealing ring 7 is provided around the distal part of the plunger 3 to provide a fluid tight seal between the plunger and the inner wall of the barrel. A reservoir chamber 6 is defined in a distal part of the plunger 3 by a plug 10 which is recessed into the hollow body of the plunger 2. The plug 10 is sealably engaged with the inner wall of the hollow body by means of a sealing ring 12 creating a fluid tight seal for the plug 10. The vacuum chamber 5 is defined by the distal end of the plunger 3 that comprises a valve 11 for controlling a fluid connection between the reservoir chamber 6 and the vacuum chamber 5. The valve 11 comprises an axially displaceable element 31 which is illustrated in more detail in FIG. 3.

FIG. 1B shows the proximal part of the syringe 1 where a locking element 13 is snap fitted to the proximal end of the plunger 2 restricting that the plunger 2 can be moved in a distal direction into the barrel 2. The barrel 2 comprises vacuum bypass channels 9 for use when freeze-drying and vacuum expanding a substance inside the vacuum chamber 5. The locking element 13 is provided with longitudinal protrusions 14 adapted to match the vacuum bypass channels 9 in the barrel 2. The locking element 13 is a rigid plastic element that grabs the proximal part of the plunger 3 and the rigidity and the extension of the locking element 13 locks the plunger 3 in an axial position relative to the barrel 2 defined by the length of the locking element 13. The locking element 13 does not prevent the plunger 3 from moving in a proximal direction out of the barrel 2. However, when a vacuum is retained in the vacuum chamber 5 the lower pressure of the vacuum will draw the plunger 3 towards the vacuum chamber 5. I.e. the syringe is configured such that the plunger 3 can be locked in the barrel 2, i.e. restricted from longitudinal/axial movement in both the proximal and distal direction. The longitudinal protrusions 14 in the locking element 13 adapted to match the vacuum bypass channels 9 in the barrel 2 provide a rotational lock of the locking element 13 in this locked configuration helping to ensure that the syringe cannot be easily tampered with in the locked configuration.

FIGS. 2A and 2B shows the syringe 1 in a prefilled condition with a first substance in the form of a solid 15 (e.g. freeze-dried paste) in the vacuum chamber 5 and a second substance in the form of a liquid 16 (e.g. water) in the reservoir chamber. FIG. 2A shows the syringe in the storage condition, i.e. prefilled with liquid and solid and where a vacuum is retained in the vacuum chamber. A locking element 13 fixes the plunger 3 and the sealed plug 10 retains the liquid in the reservoir chamber. The plug is recessed into the hollow body 19 of the plunger 3 and is thereby practically inaccessible in this storage condition of the syringe 1. The outlet 4 of the barrel is sealably closed with a connector cap 18 matching the threaded connector portion 10. In FIG. 2A the valve 11 is in a closed configuration ensuring that there is no fluid or liquid connection between the liquid 16 in the reservoir chamber 16 and the solid 15 retained under vacuum in the vacuum chamber 5. The valve 11 comprises an axially displaceable element 31 which is illustrated in further detail in FIG. 3. The displaceable element 31 comprises an enlarged contact surface 32 in the distal end that protrudes into the vacuum chamber 5. As seen in FIG. 2A there is a gap between the distal part 32 of the valve 11 and the proximal end of the solid 15. This gap is maintained by the fixed position of the plunger 3.

FIG. 2B corresponds to FIG. 2A shortly after the locking element 13 has been removed from the plunger 3. The vacuum immediately draws the plunger 3 in a distal direction closing the gap between the distal part 32 of the valve 11 and the proximal end of the solid. This distal movement and the contact between enlarged contact surface 32 and the solid forces the displaceable element 31 in the proximal direction causing the proximal part 36 of the displaceable element 31 to protrude into the reservoir chamber containing the liquid. This axial proximal movement of the displaceable element 31 opens the valve 11 to establish a fluid connection between the reservoir chamber 6 and the vacuum chamber 5. FIG. 2B is an illustration of the moment where the fluid connection is established. Immediately thereafter the liquid 16 in the reservoir chamber 6 starts to flow into the vacuum chamber 5 via channels 33 in the displaceable element 31. If a vacuum is present in the vacuum chamber 5 the liquid is sucked into the vacuum chamber 5 upon establishment of the fluid connection. Concurrently with the liquid 16 being sucked into the vacuum chamber 5 the plug 10 is gradually axially displaced in the distal direction due to the suction thereby minimizing and emptying the reservoir chamber 6. When the plug 10 reaches the distal end of the plunger 3 it may engage the displaceable element 31 and move it axially in the distal direction thereby again closing the valve 11. Both liquid 16 and solid 15 is subsequently present in the vacuum chamber and the valve 11 may be closed again such that the vacuum chamber 5 is a closed container. In the case of a freeze-dried paste the paste will quickly reconstitute and form the final flowable paste in the vacuum chamber 5 which can be delivered through the outlet 4 (upon removal of the connector cap 18) by manually controlling the plunger 3 and holding the syringe 1 via the finger grip 8.

Figure 3A:
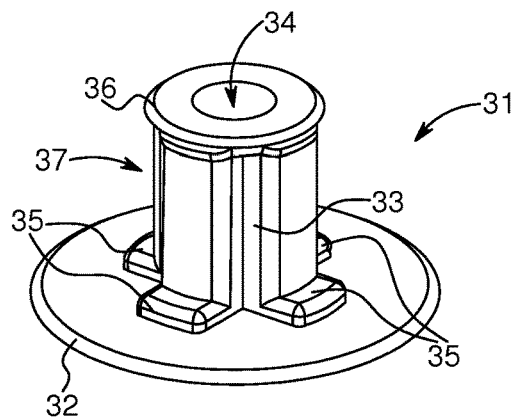
FIG. 3A shows a perspective view of the axially displaceable element of the valve of the syringe disclosed in FIGS. 1 and 2.
Figure 3B:
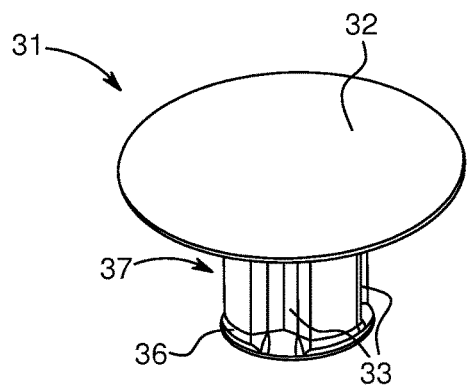
FIG. 3B shows the bottom (distal) end of the axially displaceable element in FIG. 3A.
Figure 3C:
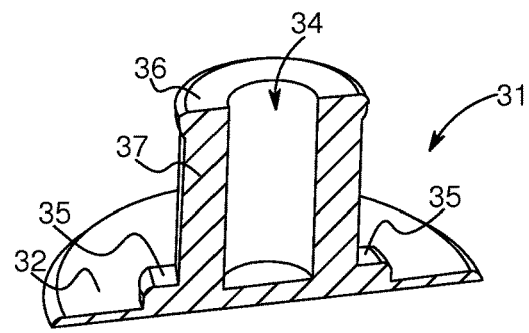
FIG. 3C shows a longitudinal cut-through illustration of the axially displaceable element in FIG. 3A.
Figure 3D:
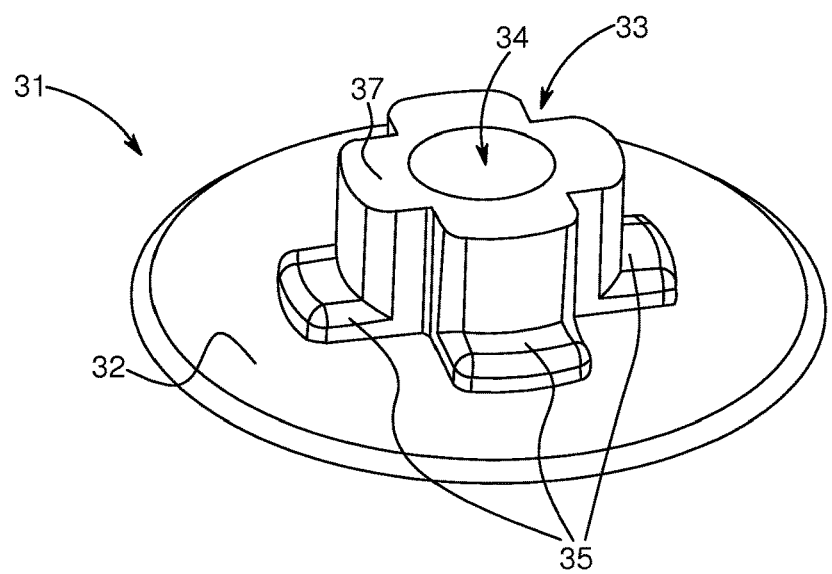
FIG. 3D shows a transverse cut-through illustration of the axially displaceable element in FIG. 3A.
Figure 3E:
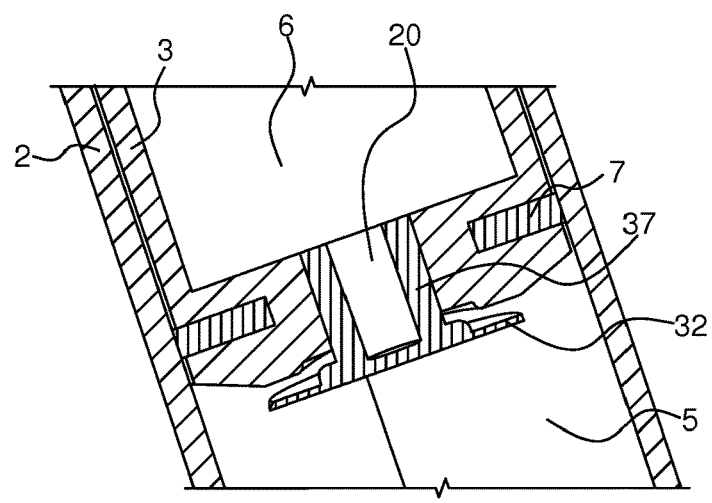
FIG. 3E shows the axially displaceable element of FIG. 3A mounted in the valve of the syringe of FIGS. 1 and 2.

There are different ways of forming a valve 11 for controlling the fluid connection between the reservoir chamber 6 and the vacuum chamber 5. In the syringe 1 disclosed in the drawings the valve is exemplified by means of the axially displaceable element 31, which is illustrated in further detail in FIG. 3. The displaceable element 31 comprises a cylindrical hollow housing 37 with proximal end 36 adapted for protruding into the reservoir chamber 6 in the open configuration of the valve 11 and a distal end 32 adapted for protruding into the vacuum chamber 5. The distal end 32 is formed as a closed plane surface with a diameter which is substantially larger than the diameter of the cylindrical housing 37, such as double or triple diameter. The proximal end 36 is formed as a ring 36 protruding from the cylindrical housing with a diameter of the ring 36 slightly larger than the diameter of the cylindrical housing 37. The (cylindrical) hole 34 makes the cylindrical housing hollow, but the hole 34 is blocked in the distal end by the distal surface 32 as seen in FIG. 3C. The hole 34 is adapted to match a corresponding longitudinal cylindrical valve element 20 mounted in the distal end of the plunger. The axial displacement of the displaceable element 31 is provided by means of the engagement between the hole 34 and the longitudinal valve element 20.

The cylindrical housing 37 of the displaceable element 31 is provided with one or more channels 33 in the form of longitudinal recessions along the length of the housing 37, these channels providing the fluid connection between the reservoir chamber and the vacuum chamber in the open configuration of the valve 11. The displaceable element 31 further comprises anti-closing protrusions 35 protruding from distal surface 32 circumferentially around the housing 37. The channels 33 are recessed into the housing 37 between these anti-closing protrusions. These anti-closing protrusions 35 are adapted to form stopping elements to prevent that the valve 11 can be closed if the axially displaceable part 31 is moved in a proximal direction, i.e. to ensure that a solid 15 expanding in the vacuum chamber 5 cannot incidentally close the valve 11 by pushing the displaceable part 31 toward the reservoir chamber 6.

Figure 4A:
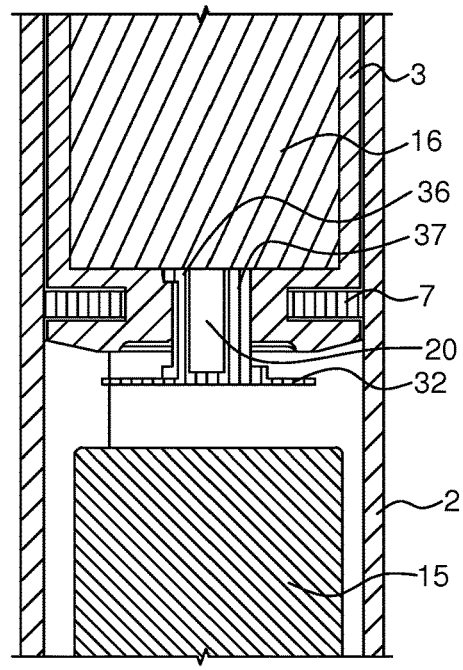
FIG. 4A shows a close up illustration of the valve of the syringe in FIGS. 1 and 2 in a closed configuration.

The operation of the valve 11 is illustrated in further detail in the close ups in FIG. 4. In FIG. 4A the valve is in a closed configuration with a solid 15 retained under vacuum in the vacuum chamber 5. The displaceable element 31 protrudes into the vacuum chamber with the distal surface 32. In the closed configuration the displaceable element 31 does not protrude into the reservoir chamber 6 where a liquid 16 is retained. The proximal ring 36 is recessed into the distal end of the plunger 3 thereby blocking any fluid connection between the liquid 16 and the solid 15, i.e. the distal end of the plunger comprises a recession formed to match the shape of the proximal ring 36. A vacuum in the vacuum chamber 5 helps to retain the displaceable part 31 in this closed configuration because the vacuum draws the displaceable element 31 in a distal direction towards the vacuum chamber 5. As seen in FIG. 4A there is a gap between the solid 15 and the distal surface 32.

Figure 4B:
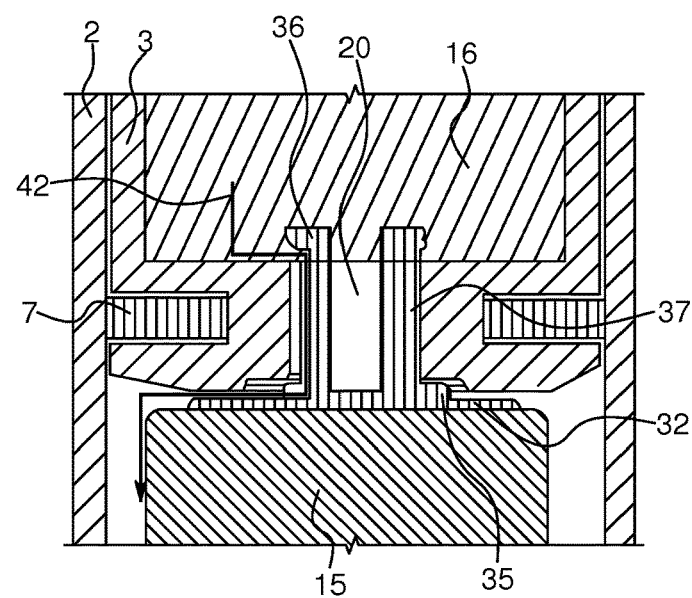
FIG. 4B shows a close up illustration of the valve of the syringe in FIGS. 1 and 2 in an open configuration, where a fluid connection between the chambers is established.

In FIG. 4B the syringe 1 has been unlocked by removing the locking element 13 and the plunger 3 is immediately drawn in a distal direction closing the gap between the distal surface 32 and the solid 15. The force exerted by this movement due to the vacuum causes the solid to engage the distal surface 32 resulting in a proximal movement of the displaceable element 31. The proximal ring 36 thereby protrudes into the reservoir chamber 6 retaining the liquid 16. This exposes the channels 33 thereby establishing a fluid (and liquid) connection between the reservoir chamber 6 and the vacuum chamber 6. The liquid 16 in the reservoir chamber 6 is resultantly immediately drawn into the vacuum chamber 6 due to the vacuum and a mixing between the two substances 15, 16 can take place in the vacuum chamber 5. The passageway of the liquid in indicated in FIG. 4B by the white arrow 42.

When the plunger 3 is drawn in a distal direction towards the solid 15, and in a case of a vacuum expanding paste 15 in the vacuum chamber 5, the solid 15 will exert a pressure on the displaceable element 31 via the distal surface 32 and force the displaceable element 31 in a proximal direction towards the reservoir chamber 6. The anti-closing protrusions 35 ensure that the valve 11 cannot be closed via such a proximal movement as illustrated in FIG. 4B where the anti-closing protrusions 35 abut the plunger 3 to provide a small gap between the distal surface 32 and the distal end of the plunger 3 thereby maintaining the fluid connection 42 between the reservoir chamber 6 and the vacuum chamber 5. As also stated previously the distal surface 32 has a diameter which is substantially greater than the diameter of the housing 37 to increase the contact area between the solid 15 and the distal surface 32 and to reduce the risk of the solid 15 interfering with rest the valve, for example if the solid 15 should enter the gap between the distal surface 32 and the plunger 3, e.g. during vacuum expansion of a paste.

Vacuum bypass channels 9 are illustrated in FIG. 1B as longitudinally extending grooves in the proximal end of the barrel 2. When the plunger 3 is arranged in the barrel 2 below these vacuum bypass channels 9 the plunger 3 sealably engages the vacuum chamber 5 via the sealing ring 7. However, when the distal part of the plunger is flush with the bypass vacuum channels 9, this sealing is not tight, because a fluid connection, in particular air, can be established between the vacuum chamber 5 and the surrounding atmosphere across the plunger 3 via the vacuum bypass channels 9. I.e. during freeze-drying of a substance 15 inside the vacuum chamber 5 suction applied at the proximal end of the barrel 2 can establish a vacuum inside the vacuum chamber 5 and thereby for example expand a freeze-dried paste. At the end of the freeze-drying (and expansion process), the plunger 3 can be displaced to a position below the vacuum bypass channels 9, thereby sealably engaging the vacuum chamber 5 and subsequently retaining the freeze-dried substance 15 in a vacuum.

Syringe Retaining Vacuum Expanded Freeze Dried Paste

In WO 2014/202760 it is described that expanding a wet paste composition by vacuum, preferably low vacuum, before freeze-drying greatly enhances the reconstitution rate of said paste. Thus, a paste which has been expanded by low vacuum reconstitutes faster than a comparable dry composition, which has not been expanded by low vacuum. A paste that has been expanded by vacuum and dried reconstitutes spontaneously to form a substantially homogenous flowable paste without any mechanical mixing. For example, a vacuum expanded, dried gelatine paste composition being present in the presently disclosed syringe will reconstitute to a ready-to-use paste suitable for direct delivery to a patient without any mechanical mixing required when an aqueous medium disposed in the reservoir chamber is led into the dried composition disposed in the vacuum chamber.

Vacuum expansion expands entrapped air pockets within the paste and such expanded air pockets are retained in the dried paste composition. The presence of larger air pockets in the dry composition enables the wetting of the dry composition due to a larger contact surface area between the dried composition and the liquid. It also facilitates unhindered distribution of the liquid into the dry composition due to the formed channels.

As disclosed in WO 2014/202760 the volume of a paste aliquot is generally higher in samples being aliquoted first as opposed to last from a single batch of paste. This is thought to be due to a partial collapse of the paste occurring over time causing variations in paste density. Such variations in density can lead to undesirable variations in the reconstitution time. Vacuum expansion of the paste prior to drying is able to reduce or even eliminate such "intra-batch" variations in paste density and thus lead to consistently fast reconstitution of the dried pastes. Thus, vacuum expansion of small batches as provided by the presently disclosed syringe provides a higher degree of reproducibility with regards to the reconstitution time.

A paste may be formed when an agent in powder form is mixed with an aqueous medium. The agent may be cross-linked. The agent may a biocompatible polymer suitable for use in haemostasis and/or wound healing, such as a cross-linked haemostatic agent in powder form, for example cross-linked gelatine powder. Examples of agent and biocompatible polymers are provided in WO 2014/202760. One example is Spongostan®/Surgifoam® available from Ethicon which is a gelatine based cross-linked absorbable haemostatic sponge. It absorbs >35 g of blood/g and within 4-6 weeks it is completely absorbed in the human body.

A paste can be prepared in a container and transferred to the vacuum chamber of the presently disclosed syringe. The paste may then be expanded by subjecting the paste to a reduced pressure, i.e. to pressures below ambient pressure, i.e. usually less than 1000 mbar (a low vacuum), by connecting the syringe with paste in the vacuum chamber to a pump, e.g. in a configuration of the presently disclosed syringe where the distal end of the plunger is located adjacent the vacuum bypass channels. Vacuum expansion results in an increase in the total volume of the paste by expansion of entrapped air within interstitial pores of the wet paste. The pressure of the vacuum is selected so that the paste expands to a sufficient degree without collapsing. Thus, the pressure must not be too low, which will result in the paste collapsing. Vacuum expansion of the paste may e.g. be performed in a freeze-dryer. Subjecting a wet paste to a sub-atmospheric pressure results in an expansion of the air within the interstitial spaces (pores) of the paste, which in turn leads to an increase in the total volume of the paste and a decrease in the density of the paste. After drying of the paste composition to achieve a dried paste, the increased pore size results in increased permeability and wettability and thus an increased reconstitution rate of the dry composition. The expansion rate during vacuum expansion depends on the vacuum pump and the size of the vacuum chamber, i.e. how fast pressure in the chamber can be decreased to the desired level. With the presently disclosed syringe the volume of the vacuum chamber is relatively small and a low vacuum level can be achieved almost instantaneously, thus expansion of the paste occurs essentially instantaneously after starting the vacuum pump. The vacuum may subsequently be retained in the syringe (for subsequent storage) if the distal end of the plunger is axially displaced to a position below the vacuum bypass channels. A locking element may then be attached to the proximal part of the plunger whereby the syringe is in a locked configuration containing the vacuum expanded paste in the vacuum chamber.

Vacuum expansion must be performed at a temperature above the freezing point of the paste, e.g. at temperatures of about 0° C. to about 25° C. When the paste comprises sensitive bioactive agents, such as thrombin, vacuum expansion is preferably performed at temperatures below ambient temperatures. Further details regarding vacuum expansion of a paste are disclosed in WO 2014/202760.

When a paste has been expanded to a desired degree, the paste can be frozen by subjecting the paste to a temperature below 0° C. for a period of time sufficient for the paste to freeze. Freezing occurs without releasing the vacuum and freezing of the paste thus locks the expanded paste structure in place. Thus, further changes in pressure hereafter will not affect the volume of the frozen paste. The freezing is preferably performed in a freeze-dryer. The temperature selected for freezing the paste depends on the freezing point of the paste and/or the glass transition temperature of the paste and can be determined by the skilled person. The desired temperature of the frozen paste is approximately 5° C. less than the lowest of the freezing point of the paste and the glass transition temperature. E.g. if the freezing point of a paste is −35° C., the paste should be cooled to about −40° C. The paste may subsequently be dried.

The paste may also be freeze-dried. Freeze-drying (also known as lyophilisation and cryodesiccation) is a dehydration process typically used to preserve a perishable material or make the material more convenient for transport. Freeze-drying works by freezing the material and then reducing the surrounding pressure to allow the frozen water in the material to sublimate directly from the solid phase to the gas phase. At the end of the operation, the final residual water content in the freeze-dried product is in general very low, such as around 2% or lower. The freeze-drying process transforms the haemostatic paste into a hard "cake-like" composition, which upon addition of an adequate amount of an aqueous medium, such as water, will form a ready-to use paste spontaneously, i.e. no mechanical mixing/reconstitution is required for said paste to form.

The expanded paste may also be dried by subjecting the expanded paste (and the syringe) to an increased temperature (while upholding the vacuum) until the paste is dry. The increased temperature is typically in the range of about 30-200° C., such as about 50° C. to about 150° C.

Drying and freeze drying of the paste may be provided when the paste is retained in the vacuum chamber of the presently disclosed syringe.

The aqueous medium used to reconstitute a paste may e.g. be selected from water, saline, a calcium chloride solution, an acidic or a base solution or a buffered aqueous solution. The aqueous medium used to reconstitute a dry composition may e.g. be selected from water, saline or a calcium chloride solution. The dry composition may comprise thrombin.

The advantages of the presently disclosed syringe and the dry composition and reconstituted paste disclosed in WO 2014/202760 are numerous and include:

- Minimal time spent preparing the paste, e.g. bleeding can be stopped faster.
- Minimized risk of compromising the sterility of the paste during preparation due the internal preparation in the syringe.
- Minimized risk of making mistakes during preparation due to the extremely simple preparation of the paste.
- Optimal consistency of paste obtained every time.
- Reliable and consistent reconstitution within a short time period.
- No sharps injury of personnel during handling
- Bioactive agents, which are unstable in solution may be added to the paste prior to drying and will thus be present in the dry composition of the invention. For example, thrombin may be added to the paste prior to drying, thereby avoiding the time-consuming and error-prone thrombin dilution steps.
- Minimises Operation Room costs since preparation of the flowable paste is so simple and fast that there is no reason to pre-prepare haemostatic flowables before surgery which may not be used.

All of the above factors lead to increased patient safety.

Further Details

The presently disclosed syringe will now be described in further detail with reference to the following items.

1. A syringe for retaining and/or mixing first and second substances comprising
   a barrel comprising a vacuum chamber for holding a first substance,
   a plunger incorporating a reservoir chamber for holding a second substance and configured to be axially displaced in the vacuum chamber, and
   a valve for controlling and/or establishing a fluid connection between the vacuum chamber and the reservoir chamber,
   wherein the syringe is configured such that
   in a first configuration the first substance can be retained under vacuum in the vacuum chamber, and
   in a second configuration the valve provides a fluid passageway between the reservoir chamber and the vacuum chamber.

2. A syringe for retaining and mixing first and second substances comprising
   a barrel comprising a sealable and/or closable distal outlet and a vacuum chamber for holding a first substance,
   a plunger for sealable engagement inside the barrel and configured to be axially displaced in relation to the vacuum chamber, the plunger incorporating a reservoir chamber for holding a second substance, and
   a valve separating the vacuum chamber inside the barrel and the reservoir chamber inside the plunger, the valve configured for controlling and/or establishing a fluid connection between the vacuum chamber and the reservoir chamber,
   wherein the syringe is configured such that
   in a first configuration corresponding to a first locked axial position of the plunger inside the barrel, the first substance can be retained under vacuum in the vacuum chamber, and
   in a second configuration the plunger is unlocked and the vacuum in the vacuum chamber draws the plunger in a distal axial direction such that the valve is engaged to provide a fluid passageway between the reservoir chamber and the vacuum chamber.

3. The syringe according to any of the preceding items, wherein the barrel comprises an open proximal end.

4. The syringe according to any of the preceding items, configured such that a proximal end of the plunger extends through an open proximal end of the barrel.

5. The syringe according to any of the preceding items, configured such that the plunger can be axially displaced through an open proximal end of the barrel.

6. The syringe according to any of the preceding items, wherein the barrel comprises a sealable/closable outlet, such as a Luer type outlet.

7. The syringe according to any of the preceding items, wherein the barrel comprises a sealable/closable outlet located at the distal end of the barrel.

8. The syringe according to any of the preceding items, wherein the outlet comprises a connector portion at a distal end, such as a Luer type connector portion.

9. The syringe according to any of the preceding items, wherein the first configuration corresponds to a first axial position of the plunger in the barrel.

10. The syringe according to any of the preceding items, wherein the second configuration corresponds to a second axial position of the plunger in the barrel.

11. The syringe according to any of the preceding items, configured such that the plunger is locked in said first configuration.

12. The syringe according to any of the preceding items, configured such that the plunger is restricted from axial displacement in said first configuration.

13. The syringe according to any of the preceding items, configured such that the plunger is restricted from axial displacement in a distal direction in said first configuration.

14. The syringe according to any of the preceding items, further comprising a removable locking element for locking the plunger in said first configuration.

15. The syringe according to any of the preceding items 14, wherein the locking element is adapted to be removably attached to a part of the plunger which extends from the proximal end of the barrel.

16. The syringe according to any of the preceding items, further comprising a sealed engagement between the plunger and barrel.

17. The syringe according to any of the preceding items, wherein the valve is located in the distal end of the plunger.

18. The syringe according to any of the preceding items, configured such that upon unlocking the plunger, a vacuum in the vacuum chamber causes an axial displacement of the plunger from a first position to a second position.

19. The syringe according to any of the preceding items, configured such that an axial displacement of the plunger from a first position to a second position engages the valve to establish a fluid passageway between the reservoir chamber and the vacuum chamber.
20. The syringe according to any of the preceding items, wherein the plunger is hollow.
21. The syringe according to any of the preceding items, wherein the reservoir chamber is defined by a hollow portion of the plunger.
22. The syringe according to any of the preceding items, wherein the reservoir chamber is located in the distal part of the plunger.
23. The syringe according to any of the preceding items, further comprising a plug inside and sealably engaged with the hollow plunger, wherein the reservoir chamber is defined by the plug inside the hollow plunger.
24. The syringe according to any of the preceding items 23, wherein the plug is completely contained within the hollow body of the plunger.
25. The syringe according to any of the preceding items 23-24, wherein the plug is recessed within the hollow body of the plunger.
26. The syringe according to any of the preceding items 23-25, wherein the plug is formed as a small plunger or piston adapted to fit and be recessed within the hollow plunger.
27. The syringe according to any of the preceding items 23-26, wherein the plug is configured to be axially displaced within the hollow body of the plunger.
28. The syringe according to any of the preceding items 23-27, wherein the plug is configured to be axially displaced distally within the hollow body of the plunger during discharge/flushing of the second substance in the reservoir chamber into the vacuum chamber.
29. The syringe according to any of the preceding items, configured such that a first substance, preferably in the form of a solid and/or dry composition, located in the vacuum chamber may engage the valve upon contact between valve and solid during axial displacement of the plunger towards the distal end of the barrel, to establish a fluid passageway between the reservoir chamber and the vacuum chamber.
30. The syringe according to any of the preceding items, wherein the reservoir chamber and the vacuum chamber are fluidly disconnected in said first configuration.
31. The syringe according to any of the preceding items, wherein the reservoir chamber and the vacuum chamber are fluidly connected in said second configuration.
32. The syringe according to any of the preceding items, wherein the valve is configured to have a closed valve configuration disconnecting the reservoir chamber and the vacuum chamber and an open valve configuration fluidly connecting the reservoir chamber and the vacuum chamber.
33. The syringe according to any of the preceding items, wherein the valve comprises at least one axially displaceable element.
34. The syringe according to any of the preceding items 33, wherein the open valve configuration corresponds to a first position of said axially displaceable element and wherein the closed valve configuration corresponds to a second position of said axially displaceable element.
35. The syringe according to any of the preceding items 33-34, wherein the valve is configured such that said axially displaceable element protrudes into the vacuum chamber in said first position and protrudes into the reservoir chamber in said second position.
36. The syringe according to any of the preceding items 33-35, wherein the valve is configured such that said axially displaceable element protrudes into the vacuum chamber and into the reservoir chamber in said open valve configuration.
37. The syringe according to any of the preceding items 33-36, wherein said axially displaceable element at a distal end comprises a plane closed surface (the distal surface) extending into the vacuum chamber, said plane surface defining a plane substantially perpendicular to the longitudinal axis of the syringe.
38. The syringe according to any of the preceding items 33-37, wherein said axially displaceable element is rotatably locked in the valve.
39. The syringe according to any of the preceding items 33-38, said axially displaceable element comprising one or more fluid bypass channels providing the fluid connection between the reservoir chamber and the vacuum chamber in the open configuration of the valve.
40. The syringe according to any of the preceding items 33-39, wherein the axially displaceable element is configured such that the valve remains in an open configuration when the axially displaceable element is displaced in the proximal direction.
41. The syringe according to any of the preceding items 33-40, wherein the axially displaceable element comprises anti-closing protrusions protruding circumferentially from the distal plane surface.
42. The syringe according to any of the preceding items 41, wherein said anti-closing protrusions are adapted to form stopping elements to prevent that the valve can be closed if the axially displaceable element is moved in a proximal direction.
43. The syringe according to any of the preceding items, wherein the syringe is prefilled with the first and second substances.
44. The syringe according to any of the preceding items, wherein the first substance is a solid, such as a dry composition.
45. The syringe according to any of the preceding items, wherein the first substance and/or the second substance is a drug.
46. The syringe according to any of the preceding items, wherein the first substance is a lyophilized substance, such as a lyophilized drug.
47. The syringe according to any of the preceding items, wherein the first substance is a paste.
48. The syringe according to any of the preceding items, wherein the first substance is a dried paste, such as a freeze-dried paste.
49. The syringe according to any of the preceding items, wherein the first substance is a dry composition being a vacuum expanded, freeze-dried paste.
50. The dry composition according to item 49, wherein the density of the freeze-dried paste is between about 1 mg/ml to about 40 mg/ml, such as between about 5 mg/ml to about 35 mg/ml, for example between about 10 mg/ml to about 35 mg/ml.
51. The syringe according to any of the preceding items, wherein the first substance is a dry composition comprising thrombin.
52. The syringe according to any of the preceding items, wherein the first substance is a dried or freeze-dried paste comprising thrombin.
53. The syringe according to any of the preceding items, wherein the second substance is a fluid, such as a liquid.

54. The syringe according to any of the preceding items, wherein the second substance is an aqueous medium selected from water, saline, a calcium chloride solution or a buffered aqueous solution.
55. The syringe according to any of the preceding items, further comprising one or more vacuum bypass channels located in the barrel and/or in the plunger.
56. The syringe according to any of preceding items 55, wherein the syringe is configured such that the plunger sealably engages the vacuum chamber in at least a first axial position of the plunger inside the vacuum chamber, and such that fluid communication is established across the plunger in at least a second axial position of the plunger inside the vacuum chamber via said one or more vacuum bypass channels.
57. The syringe according to any of preceding items 55 to 56, wherein said one or more vacuum bypass channels are configured to break the sealing between the vacuum chamber and the plunger at a predefined axial position of the plunger inside the vacuum chamber.
58. The syringe according to any of preceding items 55 to 57, wherein said one or more vacuum bypass channels are one or more longitudinal grooves formed in the inner surface of the proximal end of the vacuum chamber.
59. The syringe according to any of preceding items 55 to 58, wherein said one or more vacuum bypass channels are formed in the plunger.
60. The syringe according to any of preceding items, wherein the volume of the barrel and/or the volume of the vacuum chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.
61. The syringe according to any of preceding items, wherein the volume of the hollow body of the plunger and/or the volume of the reservoir chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.
62. The syringe according to any of preceding items, wherein the barrel, the plunger, the plug, the valve and/or the axially displaceable valve element is/are suitable for manufacture by means of single cycle injection molding.

The invention claimed is:

1. A syringe for retaining and mixing first and second substances, comprising:
   a barrel comprising a sealable and/or closable distal outlet and a vacuum chamber for holding a first substance under vacuum,
   a plunger for sealable engagement inside the barrel and configured to be axially displaced in relation to the vacuum chamber, the plunger incorporating a reservoir chamber for holding a second substance, and
   a valve separating the vacuum chamber inside the barrel and the reservoir chamber inside the plunger, the valve configured for controlling and/or establishing a fluid connection between the vacuum chamber and the reservoir chamber,
   wherein the syringe is configured such that
   in a first configuration corresponding to a first locked axial position of the plunger inside the barrel, the first substance can be retained under vacuum in the vacuum chamber such that said first configuration is a storage condition of the syringe, and
   in a second configuration the plunger is unlocked and the vacuum in the vacuum chamber draws the plunger in a distal axial direction such that the valve is engaged to provide a fluid passageway between the reservoir chamber and the vacuum chamber.

2. The syringe according to claim 1, wherein the syringe is prefilled with first and second substances and wherein the first substance is a dry composition being a vacuum expanded, freeze-dried paste, and wherein the second substance is an aqueous medium selected from water, saline, a calcium chloride solution or a buffered aqueous solution.

3. The syringe according to claim 2, wherein the freeze-dried paste comprises thrombin.

4. The syringe according to claim 1, wherein the valve is located in a distal end of the plunger.

5. The syringe according to claim 1, configured such that the plunger is restricted from axial displacement in a distal direction in said first configuration.

6. The syringe according claim 5, wherein the plunger is restricted from axial displacement in a distal direction in said first configuration by means of a removable locking element for engaging and locking the plunger in said first configuration.

7. The syringe according claim 6, wherein the locking element is adapted to be removably attached to a part of the plunger which extends from the proximal end of the barrel.

8. The syringe according to claim 4, configured such that upon unlocking the plunger, a vacuum in the vacuum chamber causes an axial displacement of the plunger from a first position to a second position.

9. The syringe according to claim 1, configured such that an axial displacement of the plunger from a first position to a second position engages the valve from a closed valve configuration in the first position to an open valve configuration in the second position to establish a fluid passageway between the reservoir chamber and the vacuum chamber.

10. The syringe according to claim 9, configured such that upon discharge of the second substance in the reservoir chamber into the vacuum chamber the valve is engaged from the open valve configuration into the closed valve configuration thereby blocking the fluid passageway between the reservoir chamber and the vacuum chamber.

11. The syringe according to claim 1, further comprising a plug inside and sealably engaged with the plunger which is hollow, such that the reservoir chamber is defined by the plug inside the hollow plunger.

12. The syringe according to claim 11, wherein the plug is completely contained within the hollow body of the plunger.

13. The syringe according to claim 11, wherein the plug is recessed within the hollow body of the plunger.

14. The syringe according to claim claims 11, wherein the plug is configured to be axially displaced distally within the hollow body of the plunger during discharge or flushing of the second substance in the reservoir chamber into the vacuum chamber.

15. The syringe according to claim 14, wherein the plug and the valve are configured such that the plug engages and closes the valve when reaching the distal end of the plunger after discharge of the second substance in the reservoir chamber.

16. The syringe according to claim 1, configured such that a first substance located in the vacuum chamber may engage the valve upon contact between valve and the first substance during axial displacement of the plunger towards the distal end of the barrel, to establish a fluid passageway between the reservoir chamber and the vacuum chamber.

17. The syringe according to claim 9, wherein the valve comprises at least one axially displaceable element and wherein the open valve configuration corresponds to a first position of said axially displaceable element and wherein the closed valve configuration corresponds to a second position of said axially displaceable element.

18. The syringe according to claim 17, wherein the valve is configured such that said axially displaceable element protrudes into the vacuum chamber in said first position and protrudes into the reservoir chamber in said second position.

19. The syringe according to claim 17, wherein said axially displaceable element at a distal end comprises a plane closed surface extending into the vacuum chamber, said plane surface defining a plane perpendicular to the longitudinal axis of the syringe.

20. The syringe according to claim 17, wherein the axially displaceable element is configured such that the valve remains in an open configuration when the axially displaceable element is displaced in the proximal direction.

21. The syringe according to claim 17, configured such that the plug inside the plunger engages the axially displaceable element and displaces it distally thereby closing the valve when reaching the distal end of the plunger after discharge of the second substance in the reservoir chamber.

22. The syringe according to claim 1, further comprising one or more vacuum bypass channels located in the barrel and/or in the plunger and configured such that the plunger sealably engages the vacuum chamber in at least a first axial position of the plunger inside the vacuum chamber, and such that fluid communication is established across the plunger in at least a second axial position of the plunger inside the vacuum chamber via said one or more vacuum bypass channels.

23. The syringe according to claim 22, wherein said one or more vacuum bypass channels are configured to break the sealing between the vacuum chamber and the plunger at a predefined axial position of the plunger inside the vacuum chamber.

24. The syringe according to claim 1, configured such that a vacuum can be generated in the vacuum chamber in a predefined configuration of the syringe by means of external vacuum generating means.

* * * * *

UNITED STATES PATENT AND TRADEMARK OFFICE
CERTIFICATE OF CORRECTION

PATENT NO. : 10,653,837 B2
APPLICATION NO. : 15/534801
DATED : May 19, 2020
INVENTOR(S) : Kristian Larsen Page 1 of 1

It is certified that error appears in the above-identified patent and that said Letters Patent is hereby corrected as shown below:

In the Claims

In Column 22, Claim 14, Line 58, delete "claims" after "claim."

Signed and Sealed this
First Day of September, 2020

Andrei Iancu
*Director of the United States Patent and Trademark Office*